United States Patent
Ryu et al.

(10) Patent No.: US 12,040,937 B2
(45) Date of Patent: *Jul. 16, 2024

(54) BEAM FAILURE DETECTION AND RECOVERY WITH CARRIER AGGREGATION

(71) Applicant: QUALCOMM Incorporated, San Diego, CA (US)

(72) Inventors: Jung Ho Ryu, Fort Lee, NJ (US); Sony Akkarakaran, Poway, CA (US); Tao Luo, San Diego, CA (US); Junyi Li, Fairless Hills, PA (US); Vasanthan Raghavan, West Windsor Township, NJ (US); Qian Zhang, Basking Ridge, NJ (US); Tianyang Bai, Somerville, NJ (US); Kiran Venugopal, Raritan, NJ (US)

(73) Assignee: QUALCOMM Incorporated, San Diego, CA (US)

( * ) Notice: Subject to any disclaimer, the term of this patent is extended or adjusted under 35 U.S.C. 154(b) by 372 days.

This patent is subject to a terminal disclaimer.

(21) Appl. No.: 17/365,891

(22) Filed: Jul. 1, 2021

(65) Prior Publication Data

US 2022/0006689 A1   Jan. 6, 2022

Related U.S. Application Data

(60) Provisional application No. 63/048,007, filed on Jul. 3, 2020.

(51) Int. Cl.
*H04L 41/0668* (2022.01)
*H04L 5/00* (2006.01)
(Continued)

(52) U.S. Cl.
CPC ........ *H04L 41/0668* (2013.01); *H04L 5/0048* (2013.01); *H04L 41/0677* (2013.01); *H04W 72/044* (2013.01)

(58) Field of Classification Search
CPC ............... H04L 41/0668; H04L 5/0048; H04L 41/0677; H04L 5/001; H04L 43/16;
(Continued)

(56) References Cited

U.S. PATENT DOCUMENTS 11,653,231 B2 *  5/2023  Zhou .................... H04B 7/0695
                                                        370/216
11,950,287 B2 *  4/2024  Zhou .................... H04W 76/27
(Continued)

OTHER PUBLICATIONS

Convida Wireless: "On Beam Failure Recovery for SCell", 3GPP Draft, 3GPP TSG-RAN WG1 #98bis, R1-1911006, On_Beam_Failure_Recovery_For_Scell, 3rd Generation Partnership Project (3GPP), Mobile Competence Centre, 650, Route Des Lucioles, F-06921, Sophia-Antipolis Cedex, France, vol. RAN WG1, No. Chongqing, China, Oct. 14, 2019-Oct. 20, 2019, Oct. 5, 2019 (Oct. 5, 2019), XP051808782, 7 pages, Retrieved from the Internet: URL: https://ftp.3gpp.org/tsg_ran/WG1_RL1/TSGR1_98b/Docs/R1-1911006.zip R1-1911006On_Beam_Failure_Recovery_for_SCell.docx [retrieved on Oct. 5, 2019], the whole document.
(Continued)

*Primary Examiner* — Hanh N Nguyen
(74) *Attorney, Agent, or Firm* — Kevin M. Donnelly; Norton Rose Fulbright US LLP

(57) ABSTRACT

This disclosure provides systems, methods, and apparatuses, including computer programs encoded on computer storage media, for wireless communication. In one aspect of the disclosure, a user equipment (UE) detects a beam failure of a first beam for a first component carrier (CC) based on a link quality associated with the first beam for the first CC. The first CC and a second CC are within a same group of
(Continued)

CCs. The UE initiates one or more beam failure recovery operations associated with any CC within the same group of CCs as the first and second CCs based on a determination of a beam failure of a second beam for the second CC. The determination is based on the detection of the beam failure for the first CC and based on the first CC and the second CC being within the same group of CCs.

30 Claims, 8 Drawing Sheets

(51) Int. Cl.
*H04L 41/0677* (2022.01)
*H04W 72/044* (2023.01)

(58) Field of Classification Search
CPC .... H04L 5/048; H04W 72/044; H04B 7/0695; H04B 7/088; H04B 7/08; A61N 1/37264; A61N 1/37282; A61N 1/37288
See application file for complete search history.

(56) References Cited

U.S. PATENT DOCUMENTS

| | | | |
|---|---|---|---|
| 2019/0173740 A1 | 6/2019 | Zhang et al. | |
| 2020/0314722 A1* | 10/2020 | Kyung | H04W 36/305 |
| 2021/0160964 A1* | 5/2021 | Sun | H04L 25/0226 |
| 2021/0297139 A1* | 9/2021 | Kwon | H04W 52/028 |
| 2022/0124819 A1* | 4/2022 | Zhang | H04B 7/0695 |
| 2022/0149922 A1* | 5/2022 | Wang | H04W 76/19 |
| 2022/0150731 A1* | 5/2022 | Li | H04B 7/0695 |
| 2022/0174774 A1* | 6/2022 | Tseng | H04W 76/23 |
| 2023/0156845 A1* | 5/2023 | Khoshnevisan | H04L 5/0053 370/216 |

OTHER PUBLICATIONS

Huawei, et al., "Discussion on SCell BFR Measurements for NR eMIMO", 3GPP Draft, 3GPP TSG-RAN WG4 Meeting #92bis, R4-1911920, 3rd Generation Partnership Project (3GPP), Mobile Competence Centre, 650, Route Des Lucioles, F-06921, Sophia-Antipolis Cedex, France, vol. RAN WG4, No. Chongqing, China, Oct. 14, 2019-Oct. 18, 2019, Oct. 4, 2019 (Oct. 4, 2019), XP051806660, 3 pages, Retrieved from the Internet: URL: https://ftp.3gpp.org/tsg_ran/WG4_Radio/TSGR4_92Bis/Docs/R4-1911920.zip R4-1911920.docx [retrieved on Oct. 4, 2019], the whole document.
Intel Corporation: "Discussion on Multi-Beam Enhancements," 3GPP Draft, 3GPP TSG RAN WG1 #98, R1-1908654, Discussion on Multi-Beam Enhancements, 3rd Generation Partnership Project (3GPP), Mobile Competence Centre, 650, Route Des Lucioles, F-06921, Sophia-Antipolis Cedex, France, vol. RAN WG1, No. Prague, CZ, Aug. 26, 2019-Aug. 30, 2019, Aug. 17, 2019 (Aug. 17. 2019), XP051765262, 16 pages, Retrieved from the Internet: URL: http://www.3gpp.org/ftp/tsg_ran/WG1_RL1/TSGR1_98/Docs/R1-1908654.zip [retrieved on Aug. 17, 2019] paragraph [0004], figure 7, chapter 2.4 chapter 4 chapter 4.1 chapter 4.2.
International Search Report and Written Opinion—PCT/US2021/040243—ISA/EPO—Dec. 20, 2021 (205995WO).
Mediatek Inc: "Enhancements on Multi-Beam Operations", 3GPP Draft, 3GPP TSG RAN WG1 #99, R1-1912135, 3rd Generation Partnership Project (3GPP), Mobile Competence Centre, 650, Route Des Lucioles, F-06921, Sophia-Antipolis, Cedex, France, vol. RAN WG1, No. Reno, USA, Nov. 18, 2019-Nov. 22, 2019, 10 Pages, Nov. 9, 2019 (Nov. 9, 2019), XP051823216, Retrieved from the Internet: URL:https://ftp.3gpp.org/tsg_ran/WG1_RL1/TSGR1_99/Docs/R1-1912135.zip, R1-1912135Multi-Beam Operation.docx [retrieved on Nov. 9, 2019] section 4, p. 6-p. 7, figure 2, chapter 2.2.1.
Huawei, et al., "Beamforming for V2X Sidelink for FR1 and FR2", 3GPP Draft, 3GPP TSG RAN WG1 Meeting #96, R1-1903075, 3rd Generation Partnership Project (3GPP), Mobile Competence Centre, 650, Route Des Lucioles, F-06921 Sophia-Antipolis Cedex, France, vol. RAN WG1, No. Athens, Greece, Feb. 25, 2019-Mar. 1, 2019, Feb. 15, 2019 (Feb. 15, 2019), XP051600771, 4 Pages, Retrieved from the Internet: URL: http://www.3gpp.org/ftp/tsg%5Fran/WG1%5FRL1/TSGR1%5F96/Docs/R1%2D1903075%2Ezip [retrieved on Feb. 15, 2019] p. 1, line 1-p. 3, line 13.
Mediatek Inc: "Enhancements on Multi-Beam Operation", 3GPP Draft, 3GPP TSG RAN WG1 #97, R1-1906537 Multi-Beam Operation_Final, 3rd Generation Partnership Project (3GPP), Mobile Competence Centre, 650, Route Des Lucioles, F-06921 Sophia-Antipolis Cedex, France, vol. RAN WG1, No. Reno, USA, May 13, 2019-May 17, 2019, May 4, 2019 (May 4, 2019), XP051708573, 13 pages, Retrieved from the internet: URL: http://www.3gpp.org/ftp/tsg%5Fran/WG1%5FRL1/TSGR1%5F97/Docs/R1%2D1906537%2Ezip, [retrieved on May 4, 2019], Section 2.1, Chapter 3.2.
Partial International Search Report—PCT/US2021/040243—ISA/EPO—Oct. 8, 2021 (205995WO).
ZTE: "Details of Latency and Overhead Reduction for Beam Management", 3GPP Draft, 3GPP TSG RAN WG1 #97, R1-1906245, Details of Latency and Overhead Reduction for Beam, 3rd Generation Partnership Project (3GPP), Mobile Competence Centre, 650, Route Des Lucioles, F-06921 Sophia-Antipolis Cede, vol. RAN WG1. No. Reno, USA, May 13, 2019-May 17, 2019, May 13, 2019 (May 13, 2019), XP051727698, 6 Pages, Retrieved from the Internet: URL: http://www.3gpp.org/ftp/Meetings%5F3GPP%5FSYNC/RAN1/Docs/R1%2D1906245%2Ezip. [retrieved on May 13, 2019] the whole document.

* cited by examiner

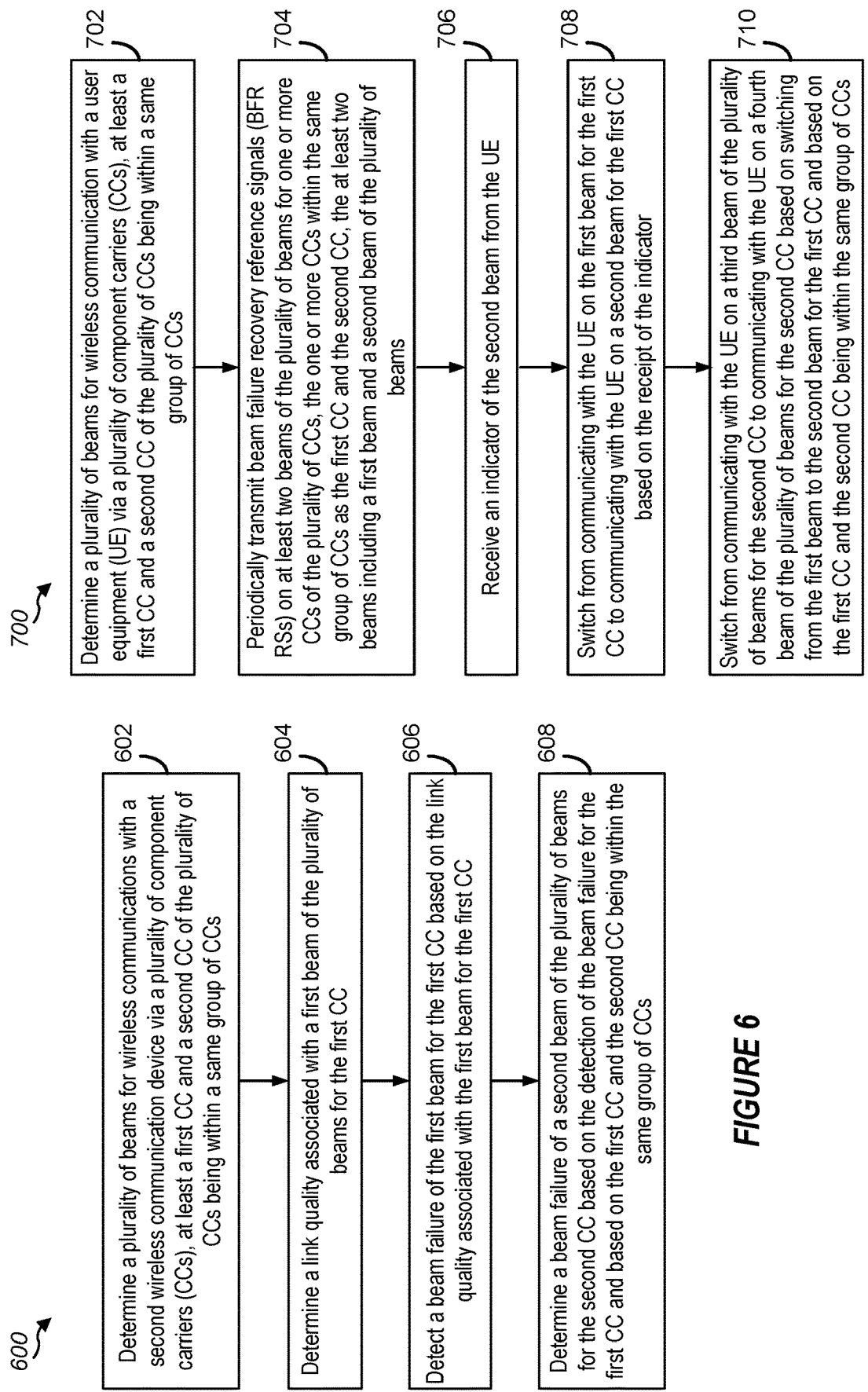

BEAM FAILURE DETECTION AND RECOVERY WITH CARRIER AGGREGATION

CROSS-REFERENCE TO RELATED APPLICATIONS

This application claims the benefit of U.S. Provisional Patent Application No. 63/048,007, entitled, "BEAM FAILURE DETECTION AND RECOVERY WITH CARRIER AGGREGATION," filed on Jul. 3, 2020, which is expressly incorporated by reference herein in its entirety.

TECHNICAL FIELD

Aspects of the present disclosure relate generally to wireless communication systems, and more particularly, to beam failure detection and beam failure recovery in wireless communication systems that support carrier aggregation.

DESCRIPTION OF THE RELATED TECHNOLOGY

Wireless communications systems are widely deployed to provide various types of communication content such as voice, video, packet data, messaging, broadcast, and so on. A wireless multiple-access communications system may include a number of base stations or network access nodes, each simultaneously supporting communication for multiple communication devices, which may be otherwise known as user equipment (UE). These systems may be capable of supporting communication with multiple UEs by sharing the available system resources (such as time, frequency, and power). Examples of such multiple-access systems include fourth generation (4G) systems such as Long Term Evolution (LTE) systems, LTE-Advanced (LTE-A) systems, or LTE-A Pro systems, and fifth generation (5G) systems which may be referred to as New Radio (NR) systems. These systems may employ technologies such as code division multiple access (CDMA), time division multiple access (TDMA), frequency division multiple access (FDMA), orthogonal frequency division multiple access (OFDMA), or discrete Fourier transform spread orthogonal frequency division multiplexing (DFT-S-OFDM).

5G NR communication systems may support wireless communications in higher frequency bands than other types of wireless communication systems. For example, 5G NR communication systems may support wireless communications in the millimeter wave (mmWave) band. In such higher frequency bands, wireless communications may be more likely to experience interference. For example, antenna beams used to communicate in the higher frequencies may experience blockages due to movement of other objects between two wireless communication devices, movement of the wireless communication devices, or reflections of the antenna beams. If a wireless channel between two wireless communication devices changes, or if one or both of the wireless communication devices move, antenna beams used to communicate between the two wireless communication devices may no longer be aligned, and the wireless communication devices need to perform beam failure detection and beam failure recovery in order to reestablish a wireless connection. If the wireless communication devices support carrier aggregation (CA) in the higher communication ranges, reestablishing the wireless connection may involve numerous operations with respect to multiple antenna beams in multiple component carriers (CCs), which increases power consumption at the wireless communication devices.

SUMMARY

The following summarizes some aspects of the present disclosure to provide a basic understanding of the discussed technology. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in summary form as a prelude to the more detailed description that is presented later.

One innovative aspect of the subject matter described in this disclosure can be implemented in a method for wireless communication performed by a user equipment (UE). The method includes detecting a beam failure of a first beam of a plurality of beams for a first component carrier (CC) of a plurality of CCs based on a link quality associated with the first beam for the first CC. The plurality of beams is for wireless communications with a second wireless communication device via the plurality of CCs. At least the first CC and a second CC of the plurality of CCs are within a same group of CCs. The method further includes initiating one or more beam failure recovery operations associated with any one or more of the plurality of CCs within the same group of CCs as the first CC and the second CC based on a determination of a beam failure of a second beam of the plurality of beams for the second CC. The determination is based on the detection of the beam failure for the first CC and based on the first CC and the second CC being within the same group of CCs.

Another innovative aspect of the subject matter described in this disclosure can be implemented in a UE. The UE includes at least one processor and a memory coupled with the at least one processor and storing processor-readable instructions that, when executed by the at least one processor, is configured to detect a beam failure of a first beam of a plurality of beams for a first CC of a plurality of CCs based on a link quality associated with the first beam for the first CC. The plurality of beams is for wireless communications with a second wireless communication device via the plurality of CCs. At least the first CC and a second CC of the plurality of CCs are within a same group of CCs. The at least one processor is further configured to initiate one or more beam failure recovery operations associated with any one or more of the plurality of CCs within the same group of CCs as the first CC and the second CC based on a determination of a beam failure of a second beam of the plurality of beams for the second CC. The determination is based on the detection of the beam failure for the first CC and based on the first CC and the second CC being within the same group of CCs.

Another innovative aspect of the subject matter described in this disclosure can be implemented in an apparatus configured for wireless communication. The apparatus includes means for detecting a beam failure of a first beam of a plurality of beams for a first CC of a plurality of CCs based on a link quality associated with the first beam for the first CC. The plurality of beams are for wireless communications with a second wireless communication device via the plurality of CCs. At least the first CC and a second CC of the plurality of CCs are within a same group of CCs. The apparatus further includes means for initiating one or more beam failure recovery operations associated with any one or more of the plurality of CCs within the same group of CCs as the first CC and the second CC based on a determination of a beam failure of a second beam of the plurality of beams for the second CC. The determination is based on the detection of the beam failure for the first CC and based on the first CC and the second CC being within the same group of CCs.

Another innovative aspect of the subject matter described in this disclosure can be implemented in a non-transitory computer-readable medium storing instructions that, when executed by a processor, cause the processor to perform operations including detecting a beam failure of a first beam of a plurality of beams for a first CC of a plurality of CCs based on a link quality associated with the first beam for the first CC. The plurality of beams are for wireless communications with a second wireless communication device via the plurality of CCs. At least the first CC and a second CC of the plurality of CCs are within a same group of CCs. The operations further include initiating one or more beam failure recovery operations associated with any one or more of the plurality of CCs within the same group of CCs as the first CC and the second CC based on a determination of a beam failure of a second beam of the plurality of beams for the second CC. The determination is based on the detection of the beam failure for the first CC and based on the first CC and the second CC being within the same group of CCs.

Another innovative aspect of the subject matter described in this disclosure can be implemented in a method for wireless communication performed by a wireless communication device. The method includes periodically transmitting beam failure recovery reference signals (BFR RSs) on at least two beams of a plurality of beams for one or more CCs of a plurality of CCs. The plurality of beams are for wireless communication with a UE via the plurality of CCs. The one or more CCs are within a same group of CCs as a first CC and a second CC of the plurality of CCs. The at least two beams include a first beam and a second beam of the plurality of beams. The method includes receiving an indicator of the second beam from the UE. The method also includes switching from communicating with the UE on the first beam for the first CC to communicating with the UE on a second beam for the first CC based on the receipt of the indicator. The method further includes switching from communicating with the UE on a third beam of the plurality of beams for the second CC to communicating with the UE on a fourth beam of the plurality of beams for the second CC based on switching from the first beam to the second beam for the first CC and based on the first CC and the second CC being within the same group of CCs.

Another innovative aspect of the subject matter described in this disclosure can be implemented in a wireless communication device. The wireless communication device includes at least one processor and a memory coupled with the at least one processor and storing processor-readable code that, when executed by the processor, is configured to periodically transmit BFR RSs on at least two beams of a plurality of beams for one or more CCs of a plurality of CCs. The plurality of beams are for wireless communication with a UE via the plurality of CCs. The one or more CCs are within a same group of CCs as a first CC and a second CC of the plurality of CCs. The at least two beams include a first beam and a second beam of the plurality of beams. The at least one processor is configured to receive an indicator of the second beam from the UE. The at least one processor is also configured to switch from communicating with the UE on the first beam for the first CC to communicating with the UE on a second beam for the first CC based on the receipt of the indicator. The at least one processor is further configured to switch from communicating with the UE on a third beam of the plurality of beams for the second CC to communicating with the UE on a fourth beam of the plurality of beams for the second CC based on switching from the first beam to the second beam for the first CC and based on the first CC and the second CC being within the same group of CCs.

Another innovative aspect of the subject matter described in this disclosure can be implemented in an apparatus configured for wireless communication. The apparatus includes means for periodically transmitting BFR RSs on at least two beams of a plurality of beams for one or more CCs of a plurality of CCs. The plurality of beams are for wireless communication with a UE via the plurality of CCs. The one or more CCs are within a same group of CCs as a first CC and a second CC of the plurality of CCs. The at least two beams include a first beam and a second beam of the plurality of beams. The apparatus includes means for receiving an indicator of the second beam from the UE. The apparatus also includes means for switching from communicating with the UE on the first beam for the first CC to communicating with the UE on a second beam for the first CC based on the receipt of the indicator. The apparatus further includes means for switching from communicating with the UE on a third beam of the plurality of beams for the second CC to communicating with the UE on a fourth beam of the plurality of beams for the second CC based on switching from the first beam to the second beam for the first CC and based on the first CC and the second CC being within the same group of CCs.

Another innovative aspect of the subject matter described in this disclosure can be implemented in a non-transitory computer-readable medium storing instructions that, when executed by a processor, cause the processor to perform operations including periodically transmitting BFR RSs on at least two beams of a plurality of beams for one or more CCs of a plurality of CCs. The plurality of beams are for wireless communication with a UE via the plurality of CCs. The one or more CCs are within a same group of CCs as a first CC and a second CC of the plurality of CCs. The at least two beams include a first beam and a second beam of the plurality of beams. The operations include receiving an indicator of the second beam from the UE. The operations also include switching from communicating with the UE on the first beam for the first CC to communicating with the UE on a second beam for the first CC based on the receipt of the indicator. The operations further include switching from communicating with the UE on a third beam of the plurality of beams for the second CC to communicating with the UE on a fourth beam of the plurality of beams for the second CC based on switching from the first beam to the second beam for the first CC and based on the first CC and the second CC being within the same group of CCs.

Other aspects, features, and implementations of the present disclosure will become apparent to a person having ordinary skill in the art, upon reviewing the following description of specific, example implementations of the present disclosure in conjunction with the accompanying figures. While features of the present disclosure may be described relative to particular implementations and figures below, all implementations of the present disclosure can include one or more of the advantageous features described herein. In other words, while one or more implementations may be described as having particular advantageous features, one or more of such features may also be used in accordance with the various implementations of the disclosure described herein. In similar fashion, while example implementations may be described below as device, system, or method implementations, such example implementations can be implemented in various devices, systems, and methods.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

FIG. 6 is a flow diagram illustrating an example process that supports BFD for one component carrier (CC) based on BFD for another CC within the same group of CCs according to some aspects.

FIG. 7 is a flow diagram illustrating an example process that supports BFR for one CC based on BFR for another CC within the same group of CCs according to some aspects.

Like reference numbers and designations in the various drawings indicate like elements.

DETAILED DESCRIPTION

Figure 1:
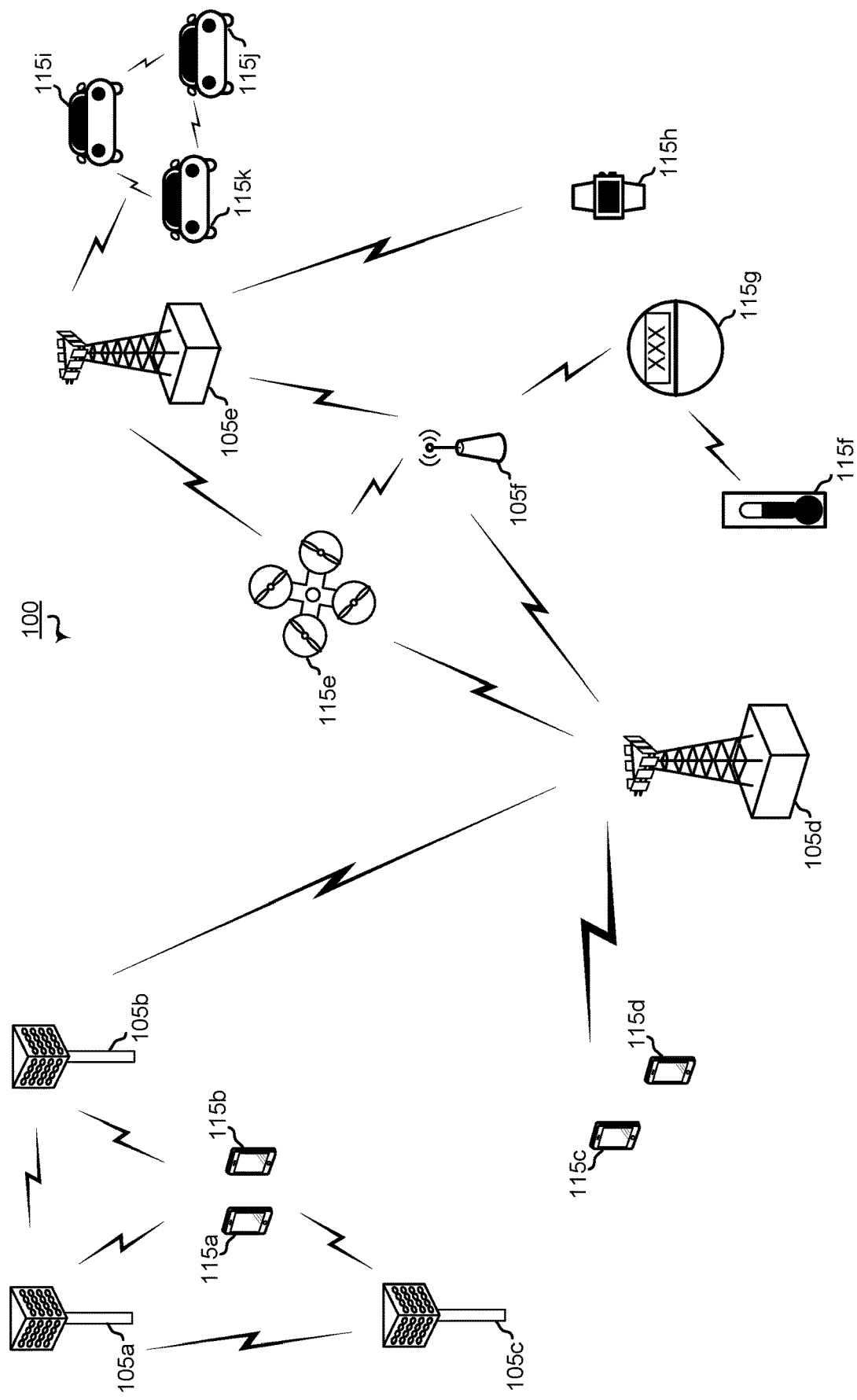
FIG. 1 is a block diagram illustrating an example wireless communication system according to some aspects.

Various aspects of the disclosure are described more fully hereinafter with reference to the accompanying drawings. This disclosure may, however, be embodied in many different forms and are not to be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art may appreciate that the scope of the disclosure is intended to cover any aspect of the disclosure disclosed herein, whether implemented independently of or combined with any other aspect of the disclosure. For example, an apparatus may be implemented or a method may be practiced using any quantity of the aspects set forth herein. In addition, the scope of the disclosure is intended to cover such an apparatus or method which is practiced using other structure, functionality, or structure and functionality in addition to or other than the various aspects of the disclosure set forth herein. Any aspect of the disclosure disclosed herein may be embodied by one or more elements of a claim.

The electromagnetic spectrum is often subdivided, based on frequency (or wavelength), into various classes, bands or channels. In fifth generation (5G) new radio (NR), two initial operating bands have been identified as frequency range designations FR1 (410 MHz-7.125 GHz) and FR2 (24.25 GHz-52.6 GHz). The frequencies between FR1 and FR2 are often referred to as mid-band frequencies. Although a portion of FR1 is greater than 6 GHz, FR1 is often referred to (interchangeably) as a "Sub-6 GHz" band in various documents and articles. A similar nomenclature issue sometimes occurs with regard to FR2, which is often referred to (interchangeably) as a "millimeter wave" band/spectrum in documents and articles, despite being different than the extremely high frequency (EHF) band (30 GHz-300 GHz) which is identified by the International Telecommunications Union (ITU) as a "millimeter wave" band. With the above aspects in mind, unless specifically stated otherwise, it should be understood that the term "sub-6 GHz" or the like if used herein may broadly represent frequencies that may be less than 6 GHz, may be within FR1, or may include mid-band frequencies. Further, unless specifically stated otherwise, it should be understood that the term "millimeter wave" or the like if used herein may broadly represent frequencies that may include mid-band frequencies, may be within FR2, or may be within the EHF band.

The present disclosure provides systems, apparatus, methods, and computer-readable media for beam failure detection (BFD) and beam failure recovery (BFR) in wireless communication systems that support carrier aggregation (CA), particularly at higher frequency bands such as FR2 or the millimeter wave (mmWave) band. To illustrate, a user equipment (UE) and a wireless communication device may each use multiple respective beams for wireless communications via multiple component carriers (CCs) within a same group of CCs. The group of CCs may include multiple or all CCs in a same frequency band, such as the mmWave band, a subset of the CCs in a particular frequency band, or CCs that span multiple preselected frequency bands. In some implementations, the wireless communication device is a second UE, and the wireless communications include sidelink (SL) communications between the UE and the second UE. In some other implementations, the wireless communication device is a base station, and the wireless communications include downlink (DL) communications or uplink (UL) communications from the base station to the UE or from the UE to the base station, respectively.

The UE and the wireless communication device may be configured to detect beam failures for one CC of the multiple CCs and to automatically determine beam failures for one or more other CCs within the same group of CCs, such as CCs in the mmWave band. For example, the wireless communication device may be configured to periodically transmit beam failure detection reference signals (BFD RSs) on one or more beams for a first CC. The UE may receive the BFD RSs on at least a first beam for the first CC and, based on measurements of the BFD RSs, the UE may detect failure of the first beam for the first CC. As used herein, a "beam failure" or "failure of a beam" may refer to an instance in which the UE determines that the signal strengths of messages received on the beam no longer satisfy a threshold. As such case, the UE may determine that another beam is preferable to enable communication between the UE and the wireless communication device. Additionally, the UE may determine a failure of a second beam for a second CC based on detection of the failure of the first beam for the first CC and based on the first CC and the second CC being within the same group of CCs. Thus, the UE may detect failure of a beam in one CC within a group of CCs, and based on the detected failure, the UE may determine failure of one or more other beams for one or more other CCs within the same group of CCs without requiring the performance of respective measurements for the one or more other beams. The wireless communication device may perform similar operations. For example, the UE may periodically transmit BFD RSs to the wireless communication device on one or more beams of the second CC, or another CC within the same group of CCs, and the wireless communication device may detect a beam failure for the second CC and automatically determine beam failures for one or more other CCs within the same group of CCs. In some implementations, the UE may transmit the BFD RSs to the wireless communication device on one or more beams for the second CC (or other CCs) concurrently with monitoring for BFD RSs from the wireless communication device on one or more beams for the first CC. Alternatively, the UE may monitor for BFD RSs from the wireless communication device on one or more beams for the first CC during some time periods, and the UE may transmit BFD RSs to the wireless communication device on one or more beams for the first CC during other time periods, such that the UE is configured for BFD RS reception and BFD RS transmission according to different schedules.

After detecting the failure of the first beam for the first CC, the UE may monitor for beam failure recovery reference signals (BFR RSs) from the wireless communication device. The UE may identify a strongest beam associated with a received BFR RS and may switch from communicating with the wireless communication device on the first beam for the first CC to communicating with the wireless communication device on the strongest beam (a third beam) for the first CC. The UE may also switch from communicating with the wireless communication device on the second beam for the second CC to communicating with the wireless communication device on a fourth beam for the second CC based on switching the beam for the first CC. Thus, the UE may switch beams in one CC within a group of CCs based on measurements of BFR RSs, and based on the switching, the UE may switch one or more beams for one or more other CCs within the same group of CCs without performing respective measurements on BFR RSs. Additionally, the UE may transmit an indicator of the third beam to the wireless communication device, and the wireless communication device may switch beams for communicating with the UE for the first CC based on the indicator and may switch beams for communicating with the UE for one or more other CCs within the same group of CCs based on the switching for the first CC. In some implementations, the UE may periodically transmit BFR RSs to the wireless communication device on a respective beam or beams for one or more other CCs within the same group of CCs, and the wireless communication device may switch beams in a similar manner to as described above for the UE.

Particular implementations of the subject matter described in this disclosure can be implemented to realize one or more of the following potential advantages. In some aspects, the present disclosure provides for automatic determination of beam failures for one or more CCs within a group of CCs, such as CCs within a same frequency band or CCs spanning multiple frequency bands, based on detection of a beam failure for one CC within the same group of CCs. For example, a UE may detect a beam failure for a first CC based on measurements of BFD RSs from a wireless communication device, and the UE may determine a beam failure for a second CC within the same group of CCs based on the detection of the beam failure for the first CC. Additionally, the present disclosure provides for automatic recovery from beam failures in one or more CCs within a same group of CCs based on recovery from a beam failure for one CC within the same group of CCs. For example, a UE may determine to switch from communicating with a wireless communication device on a first beam via a first CC to communicating with the wireless communication device on a third beam via the first CC based on measurements of BFR RSs received from the wireless communication device. The UE may also switch from communicating with the wireless communication device on a second beam for a second CC within the same group of CCs to communicating with the wireless communication device on a fourth beam for the second CC based on switching the beam for the first CC. Thus, a wireless communication device according to the present disclosure may be configured to automatically detect beam failures and to switch beams for one or more other CCs based on a detected failure and beam switching performed for one CC within the same group of CCs, which reduces the amount of signal measuring and processing at the wireless communication device as compared to detecting beam failures and switching beams for each CC within the same group of CCs based on respective reference signal measurements. Reducing the amount of signal measuring and processing reduces power consumption at the wireless communication device. The systems and techniques of the present disclosure may be particularly advantageous for reducing power consumption at UEs that communicate using CA over a SL at higher frequencies, such as the mmWave band.

This disclosure relates generally to providing or participating in authorized shared access between two or more wireless communications systems, also referred to as wireless communications networks. In various implementations, the techniques and apparatus may be used for wireless communication networks such as code division multiple access (CDMA) networks, time division multiple access (TDMA) networks, frequency division multiple access (FDMA) networks, orthogonal FDMA (OFDMA) networks, single-carrier FDMA (SC-FDMA) networks, LTE networks, GSM networks, 5th Generation (5G) or new radio (NR) networks (sometimes referred to as "5G NR" networks, systems, or devices), as well as other communications networks. As described herein, the terms "networks" and "systems" may be used interchangeably.

A CDMA network may implement a radio technology such as universal terrestrial radio access (UTRA), cdma2000, and the like. UTRA includes wideband-CDMA (W-CDMA) and low chip rate (LCR). CDMA2000 covers IS-2000, IS-95, and IS-856 standards.

A TDMA network may implement a radio technology such as Global System for Mobile Communications (GSM). 3GPP defines standards for the GSM EDGE (enhanced data rates for GSM evolution) radio access network (RAN), also denoted as GERAN. GERAN is the radio component of GSM or GSM EDGE, together with the network that joins the base stations (for example, the Ater and Abis interfaces, among other examples) and the base station controllers (for example, A interfaces, among other examples). The radio access network represents a component of a GSM network, through which phone calls and packet data are routed from and to the public switched telephone network (PSTN) and Internet to and from subscriber handsets, also known as user terminals or user equipments (UEs). A mobile phone operator's network may include one or more GERANs, which may be coupled with UTRANs in the case of a UMTS or GSM network. Additionally, an operator network may include one or more LTE networks, or one or more other networks. The various different network types may use different radio access technologies (RATs) and radio access networks (RANs).

An OFDMA network may implement a radio technology such as evolved UTRA (E-UTRA), IEEE 802.11, IEEE 802.16, IEEE 802.20, flash-OFDM and the like. UTRA, E-UTRA, and GSM are part of universal mobile telecommunication system (UMTS). In particular, long term evolution (LTE) is a release of UMTS that uses E-UTRA. UTRA, E-UTRA, GSM, UMTS and LTE are described in documents provided from an organization named the "3rd Generation Partnership Project" (3GPP), and cdma2000 is described in documents from an organization named "3rd Generation Partnership Project 2" (3GPP2). These various radio technologies and standards are known or are being developed. For example, the 3GPP is a collaboration between groups of telecommunications associations that aims to define a globally applicable third generation (3G) mobile phone specification. 3GPP long term evolution (LTE) is a 3GPP project aimed at improving the universal mobile telecommunications system (UMTS) mobile phone standard. The 3GPP may define specifications for the next generation of mobile networks, mobile systems, and mobile devices. The present disclosure may describe certain aspects with reference to LTE, 4G, 5G, or NR technologies; however, the description is not intended to be limited to a specific technology or application, and one or more aspects described with reference to one technology may be understood to be applicable to another technology. Indeed, one or more aspects the present disclosure are related to shared access to wireless spectrum between networks using different radio access technologies or radio air interfaces.

5G networks contemplate diverse deployments, diverse spectrum, and diverse services and devices that may be implemented using an OFDM-based unified, air interface. To achieve these goals, further enhancements to LTE and LTE-A are considered in addition to development of the new radio technology for 5G NR networks. The 5G NR will be capable of scaling to provide coverage (1) to a massive Internet of things (IoTs) with an ultra-high density (such as ~1M nodes per km2), ultra-low complexity (such as ~10s of bits per sec), ultra-low energy (such as ~10+ years of battery life), and deep coverage with the capability to reach challenging locations; (2) including mission-critical control with strong security to safeguard sensitive personal, financial, or classified information, ultra-high reliability (such as ~99.9999% reliability), ultra-low latency (such as ~1 millisecond (ms)), and users with wide ranges of mobility or lack thereof; and (3) with enhanced mobile broadband including extreme high capacity (such as ~10 Tbps per km2), extreme data rates (such as multi-Gbps rate, 100+ Mbps user experienced rates), and deep awareness with advanced discovery and optimizations.

5G NR devices, networks, and systems may be implemented to use optimized OFDM-based waveform features. These features may include scalable numerology and transmission time intervals (TTIs); a common, flexible framework to efficiently multiplex services and features with a dynamic, low-latency time division duplex (TDD) or frequency division duplex (FDD) design; and advanced wireless technologies, such as massive multiple input, multiple output (MIMO), robust millimeter wave (mmWave) transmissions, advanced channel coding, and device-centric mobility. Scalability of the numerology in 5G NR, with scaling of subcarrier spacing, may efficiently address operating diverse services across diverse spectrum and diverse deployments. For example, in various outdoor and macro coverage deployments of less than 3 GHz FDD or TDD implementations, subcarrier spacing may occur with 15 kHz, for example over 1, 5, 10, 20 MHz, and the like bandwidth. For other various outdoor and small cell coverage deployments of TDD greater than 3 GHz, subcarrier spacing may occur with 30 kHz over 80 or 100 MHz bandwidth. For other various indoor wideband implementations, using a TDD over the unlicensed portion of the 5 GHz band, the subcarrier spacing may occur with 60 kHz over a 160 MHz bandwidth. Finally, for various deployments transmitting with mmWave components at a TDD of 28 GHz, subcarrier spacing may occur with 120 kHz over a 500 MHz bandwidth.

The scalable numerology of 5G NR facilitates scalable TTI for diverse latency and quality of service (QoS) requirements. For example, shorter TTI may be used for low latency and high reliability, while longer TTI may be used for higher spectral efficiency. The efficient multiplexing of long and short TTIs to allow transmissions to start on symbol boundaries. 5G NR also contemplates a self-contained integrated subframe design with uplink or downlink scheduling information, data, and acknowledgement in the same subframe. The self-contained integrated subframe supports communications in unlicensed or contention-based shared spectrum, adaptive uplink or downlink that may be flexibly configured on a per-cell basis to dynamically switch between uplink and downlink to meet the current traffic needs.

For clarity, certain aspects of the apparatus and techniques may be described below with reference to example 5G NR implementations or in a 5G-centric way, and 5G terminology may be used as illustrative examples in portions of the description below; however, the description is not intended to be limited to 5G applications.

Moreover, it should be understood that, in operation, wireless communication networks adapted according to the concepts herein may operate with any combination of licensed or unlicensed spectrum depending on loading and availability. Accordingly, it will be apparent to a person having ordinary skill in the art that the systems, apparatus and methods described herein may be applied to other communications systems and applications than the particular examples provided.

FIG. 1 is a block diagram illustrating an example of a wireless communication system according to some aspects. The wireless communication system may include wireless network 100. The wireless network 100 may, for example, include a 5G wireless network. As appreciated by those skilled in the art, components appearing in FIG. 1 are likely to have related counterparts in other network arrangements including, for example, cellular-style network arrangements and non-cellular-style-network arrangements, such as device-to-device, peer-to-peer or ad hoc network arrangements, among other examples.

The wireless network 100 illustrated in FIG. 1 includes a number of base stations 105 and other network entities. A base station may be a station that communicates with the UEs and may be referred to as an evolved node B (eNB), a next generation eNB (gNB), an access point, and the like. Each base station 105 may provide communication coverage for a particular geographic area. In 3GPP, the term "cell" can refer to this particular geographic coverage area of a base station or a base station subsystem serving the coverage area, depending on the context in which the term is used. In implementations of the wireless network 100 herein, the base stations 105 may be associated with a same operator or different operators, such as the wireless network 100 may include a plurality of operator wireless networks. Additionally, in implementations of the wireless network 100 herein, the base stations 105 may provide wireless communications using one or more of the same frequencies, such as one or more frequency bands in licensed spectrum, unlicensed spectrum, or a combination thereof, as a neighboring cell. In some examples, an individual base station 105 or UE 115 may be operated by more than one network operating entity. In some other examples, each base station 105 and UE 115 may be operated by a single network operating entity.

A base station may provide communication coverage for a macro cell or a small cell, such as a pico cell or a femto cell, or other types of cell. A macro cell generally covers a relatively large geographic area, such as several kilometers in radius, and may allow unrestricted access by UEs with service subscriptions with the network provider. A small cell, such as a pico cell, would generally cover a relatively smaller geographic area and may allow unrestricted access by UEs with service subscriptions with the network provider. A small cell, such as a femto cell, would also generally cover a relatively small geographic area, such as a home, and, in addition to unrestricted access, may provide restricted access by UEs having an association with the femto cell, such as UEs in a closed subscriber group (CSG), UEs for users in the home, and the like. A base station for a macro cell may be referred to as a macro base station. A base station for a small cell may be referred to as a small cell base station, a pico base station, a femto base station or a home base station. In the example shown in FIG. 1, base stations 105d and 105e are regular macro base stations, while base stations 105a-105c are macro base stations enabled with one of 3 dimension (3D), full dimension (FD), or massive MIMO. Base stations 105a-105c take advantage of their higher dimension MIMO capabilities to exploit 3D beamforming in both elevation and azimuth beamforming to increase coverage and capacity. Base station 105f is a small cell base station which may be a home node or portable access point. A base station may support one or multiple cells, such as two cells, three cells, four cells, and the like.

The wireless network 100 may support synchronous or asynchronous operation. For synchronous operation, the base stations may have similar frame timing, and transmissions from different base stations may be approximately aligned in time. For asynchronous operation, the base stations may have different frame timing, and transmissions from different base stations may not be aligned in time. In some scenarios, networks may be enabled or configured to handle dynamic switching between synchronous or asynchronous operations.

The UEs 115 are dispersed throughout the wireless network 100, and each UE may be stationary or mobile. It should be appreciated that, although a mobile apparatus is commonly referred to as user equipment (UE) in standards and specifications promulgated by the 3GPP, such apparatus may additionally or otherwise be referred to by those skilled in the art as a mobile station (MS), a subscriber station, a mobile unit, a subscriber unit, a wireless unit, a remote unit, a mobile device, a wireless device, a wireless communications device, a remote device, a mobile subscriber station, an access terminal (AT), a mobile terminal, a wireless terminal, a remote terminal, a handset, a terminal, a user agent, a mobile client, a client, or some other suitable terminology. Within the present document, a "mobile" apparatus or UE need not necessarily have a capability to move, and may be stationary. Some non-limiting examples of a mobile apparatus, such as may include implementations of one or more of the UEs 115, include a mobile, a cellular (cell) phone, a smart phone, a session initiation protocol (SIP) phone, a wireless local loop (WLL) station, a laptop, a personal computer (PC), a notebook, a netbook, a smart book, a tablet, and a personal digital assistant (PDA). A mobile apparatus may additionally be an "Internet of things" (IoT) or "Internet of everything" (IoE) device such as an automotive or other transportation vehicle, a satellite radio, a global positioning system (GPS) device, a logistics controller, a drone, a multi-copter, a quad-copter, a smart energy or security device, a solar panel or solar array, municipal lighting, water, or other infrastructure; industrial automation and enterprise devices; consumer and wearable devices, such as eyewear, a wearable camera, a smart watch, a health or fitness tracker, a mammal implantable device, a gesture tracking device, a medical device, a digital audio player (such as MP3 player), a camera or a game console, among other examples; and digital home or smart home devices such as a home audio, video, and multimedia device, an appliance, a sensor, a vending machine, intelligent lighting, a home security system, or a smart meter, among other examples. In one aspect, a UE may be a device that includes a Universal Integrated Circuit Card (UICC). In another aspect, a UE may be a device that does not include a UICC. In some aspects, UEs that do not include UICCs may be referred to as IoE devices. The UEs 115a-115d of the implementation illustrated in FIG. 1 are examples of mobile smart phone-type devices accessing the wireless network 100. A UE may be a machine specifically configured for connected communication, including machine type communication (MTC), enhanced MTC (eMTC), narrowband IoT (NB-IoT) and the like. The UEs 115e-115k illustrated in FIG. 1 are examples of various machines configured for communication that access 5G network 100.

A mobile apparatus, such as the UEs 115, may be able to communicate with any type of the base stations, whether macro base stations, pico base stations, femto base stations, relays, and the like. In FIG. 1, a communication link (represented as a lightning bolt) indicates wireless transmissions between a UE and a serving base station, which is a base station designated to serve the UE on the downlink or uplink, or desired transmission between base stations, and backhaul transmissions between base stations. Backhaul communication between base stations of the wireless network 100 may occur using wired or wireless communication links.

In operation at the 5G network 100, the base stations 105a-105c serve the UEs 115a and 115b using 3D beamforming and coordinated spatial techniques, such as coordinated multipoint (CoMP) or multi-connectivity. Macro base station 105d performs backhaul communications with the base stations 105a-105c, as well as small cell, the base station 105f. Macro base station 105d also transmits multicast services which are subscribed to and received by the UEs 115c and 115d. Such multicast services may include mobile television or stream video, or may include other services for providing community information, such as weather emergencies or alerts, such as Amber alerts or gray alerts.

The wireless network 100 of implementations supports mission critical communications with ultra-reliable and redundant links for mission critical devices, such as the UE 115e, which is a drone. Redundant communication links with the UE 115e include from the macro base stations 105d and 105e, as well as small cell base station 105f. Other machine type devices, such as UE 115f (thermometer), the UE 115g (smart meter), and the UE 115h (wearable device) may communicate through the wireless network 100 either directly with base stations, such as the small cell base station 105f, and the macro base station 105e, or in multi-hop configurations by communicating with another user device which relays its information to the network, such as the UE 115f communicating temperature measurement information to the smart meter, the UE 115g, which is then reported to the network through the small cell base station 105f. The 5G network 100 may provide additional network efficiency through dynamic, low-latency TDD or FDD communications, such as in a vehicle-to-vehicle (V2V) mesh network between the UEs 115i-115k communicating with the macro base station 105e.

Figure 2:
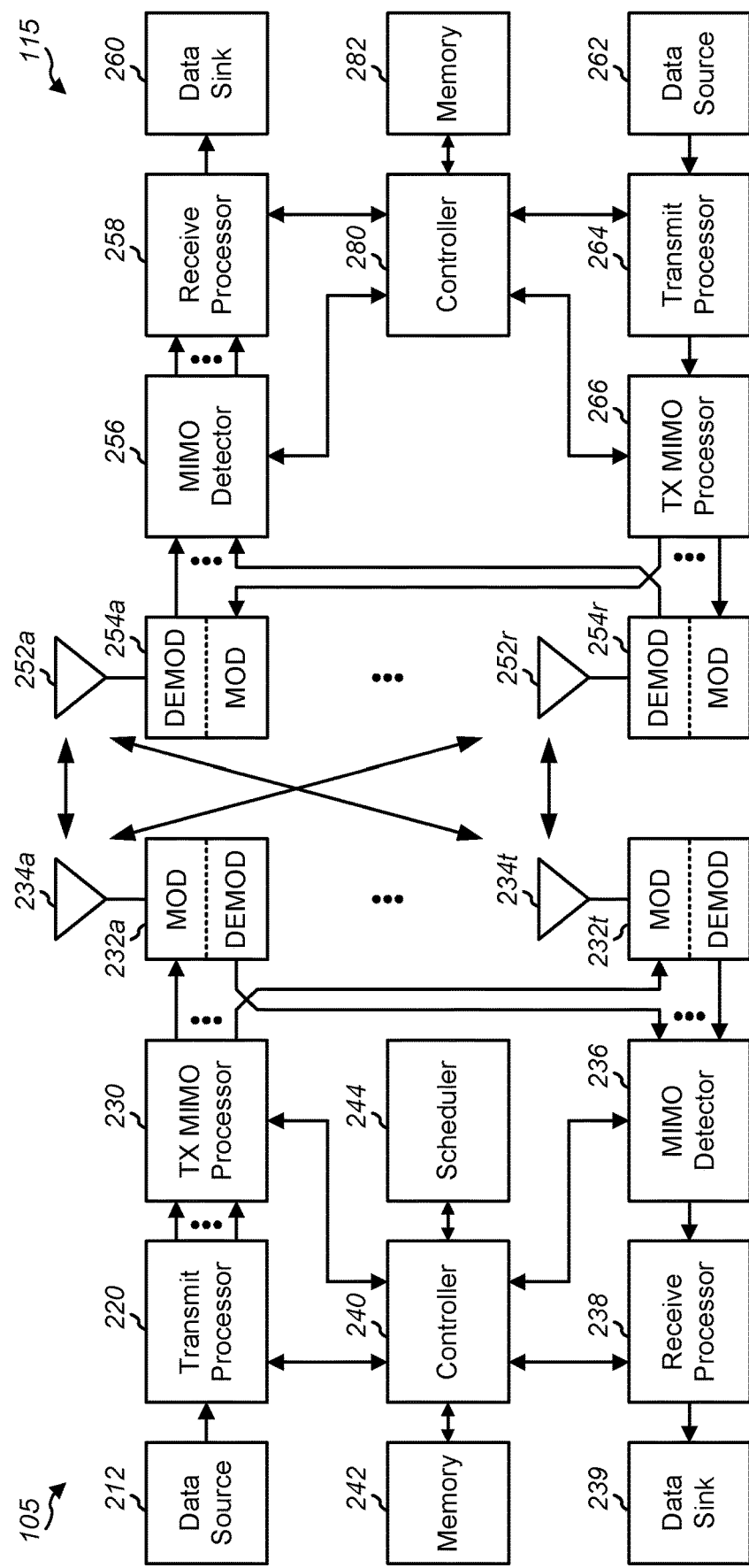
FIG. 2 is a block diagram illustrating examples of a base station and a user equipment (UE) according to some aspects.

FIG. 2 is a block diagram illustrating examples of a base station 105 and a UE 115 according to some aspects. The base station 105 and the UE 115 may be one of the base stations and one of the UEs in FIG. 1. For a restricted association scenario (as mentioned above), the base station 105 may be the small cell base station 105f in FIG. 1, and the UE 115 may be the UE 115c or 115d operating in a service area of the base station 105f, which in order to access the small cell base station 105f, would be included in a list of accessible UEs for the small cell base station 105f. Additionally, the base station 105 may be a base station of some other type. As shown in FIG. 2, the base station 105 may be equipped with antennas 234a through 234t, and the UE 115 may be equipped with antennas 252a through 252r for facilitating wireless communications.

At the base station 105, a transmit processor 220 may receive data from a data source 212 and control information from a controller 240. The control information may be for the physical broadcast channel (PBCH), physical control format indicator channel (PCFICH), physical hybrid-ARQ (automatic repeat request) indicator channel (PHICH), physical downlink control channel (PDCCH), enhanced physical downlink control channel (EPDCCH), or MTC physical downlink control channel (MPDCCH), among other examples. The data may be for the PDSCH, among other examples. The transmit processor 220 may process, such as encode and symbol map, the data and control information to obtain data symbols and control symbols, respectively. Additionally, the transmit processor 220 may generate reference symbols, such as for the primary synchronization signal (PSS) and secondary synchronization signal (SSS), and cell-specific reference signal. Transmit (TX) multiple-input multiple-output (MIMO) processor 230 may perform spatial processing on the data symbols, the control symbols, or the reference symbols, if applicable, and may provide output symbol streams to modulators (MODs) 232a through 232t. For example, spatial processing performed on the data symbols, the control symbols, or the reference symbols may include precoding. Each modulator 232 may process a respective output symbol stream, such as for OFDM, among other examples, to obtain an output sample stream. Each modulator 232 may additionally or alternatively process the output sample stream to obtain a downlink signal. For example, to process the output sample stream, each modulator 232 may convert to analog, amplify, filter, and upconvert the output sample stream to obtain the downlink signal. Downlink signals from modulators 232a through 232t may be transmitted via the antennas 234a through 234t, respectively.

At the UE 115, the antennas 252a through 252r may receive the downlink signals from the base station 105 and may provide received signals to the demodulators (DE-MODs) 254a through 254r, respectively. Each demodulator 254 may condition a respective received signal to obtain input samples. For example, to condition the respective received signal, each demodulator 254 may filter, amplify, downconvert, and digitize the respective received signal to obtain the input samples. Each demodulator 254 may further process the input samples, such as for OFDM, among other examples, to obtain received symbols. MIMO detector 256 may obtain received symbols from demodulators 254a through 254r, perform MIMO detection on the received symbols if applicable, and provide detected symbols. Receive processor 258 may process the detected symbols, provide decoded data for the UE 115 to a data sink 260, and provide decoded control information to a controller 280. For example, to process the detected symbols, the receive processor 258 may demodulate, deinterleave, and decode the detected symbols.

On the uplink, at the UE 115, a transmit processor 264 may receive and process data (such as for the physical uplink shared channel (PUSCH)) from a data source 262 and control information (such as for the physical uplink control channel (PUCCH)) from the controller 280. Additionally, the transmit processor 264 may generate reference symbols for a reference signal. The symbols from the transmit processor 264 may be precoded by TX MIMO processor 266 if applicable, further processed by the modulators 254a through 254r (such as for SC-FDM, among other examples), and transmitted to the base station 105. At base station 105, the uplink signals from the UE 115 may be received by antennas 234, processed by demodulators 232, detected by MIMO detector 236 if applicable, and further processed by receive processor 238 to obtain decoded data and control information sent by the UE 115. The receive processor 238 may provide the decoded data to data sink 239 and the decoded control information to the controller 240.

The controllers 240 and 280 may direct the operation at the base station 105 and the UE 115, respectively. The controller 240 or other processors and modules at the base station 105 or the controller 280 or other processors and modules at the UE 115 may perform or direct the execution of various processes for the techniques described herein, such as to perform or direct the execution illustrated in FIGS. 6 and 7, or other processes for the techniques described herein. The memories 242 and 282 may store data and program codes for the base station 105 and The UE 115, respectively. Scheduler 244 may schedule UEs for data transmission on the downlink or uplink.

In some cases, the UE 115 and the base station 105 may operate in a shared radio frequency spectrum band, which may include licensed or unlicensed, such as contention-based, frequency spectrum. In an unlicensed frequency portion of the shared radio frequency spectrum band, the UEs 115 or the base stations 105 may traditionally perform a medium-sensing procedure to contend for access to the frequency spectrum. For example, the UE 115 or base station 105 may perform a listen-before-talk or listen-before-transmitting (LBT) procedure such as a clear channel assessment (CCA) prior to communicating in order to determine whether the shared channel is available. A CCA may include an energy detection procedure to determine whether there are any other active transmissions. For example, a device may infer that a change in a received signal strength indicator (RSSI) of a power meter indicates that a channel is occupied. Specifically, signal power that is concentrated in a certain bandwidth and exceeds a predetermined noise floor may indicate another wireless transmitter. In some implementations, a CCA may include detection of specific sequences that indicate use of the channel. For example, another device may transmit a specific preamble prior to transmitting a data sequence. In some cases, an LBT procedure may include a wireless node adjusting its own back off window based on the amount of energy detected on a channel or the acknowledge or negative-acknowledge (ACK or NACK) feedback for its own transmitted packets as a proxy for collisions.

Figure 3:
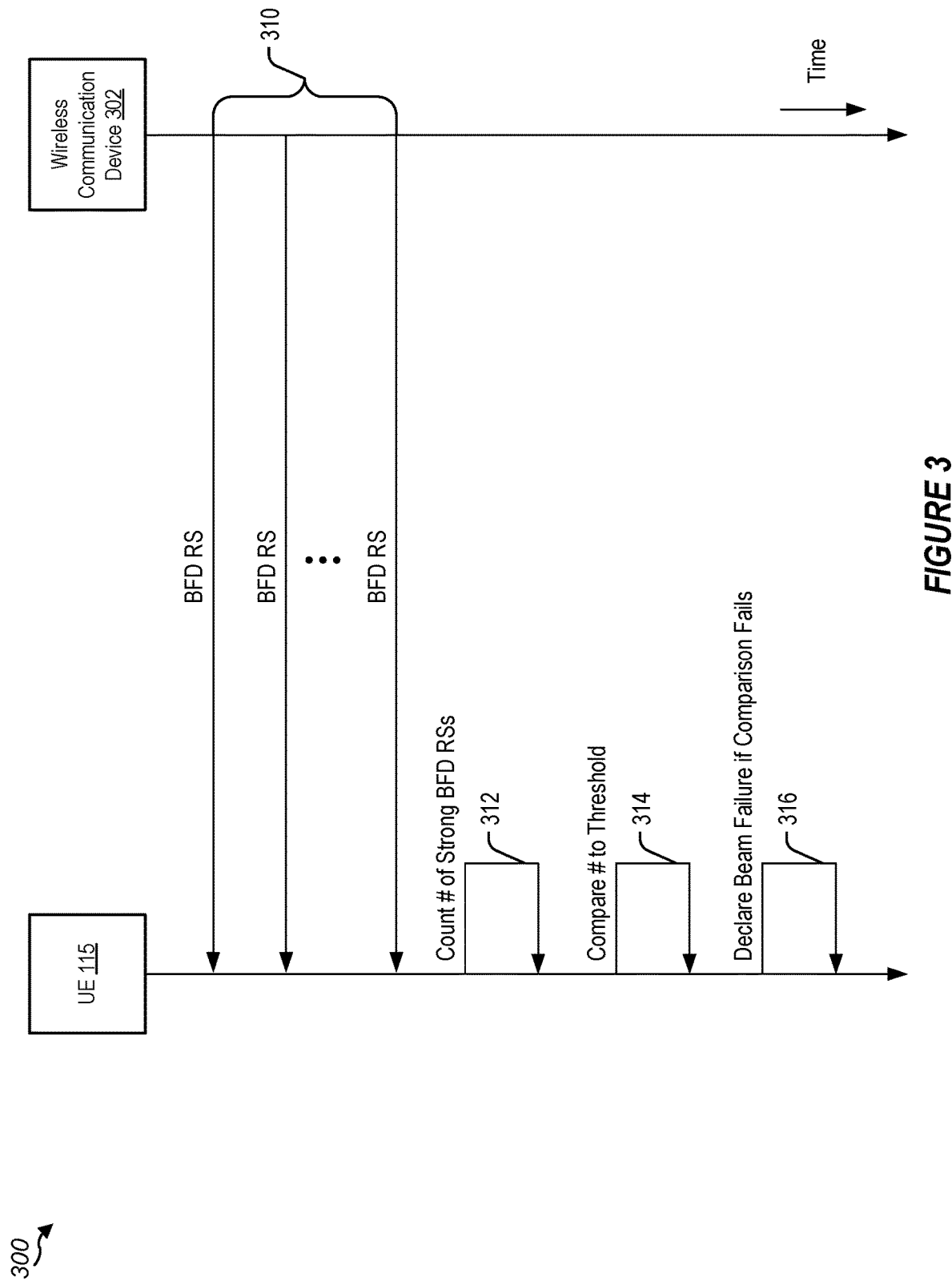
FIG. 3 is a ladder diagram illustrating an example of performing beam failure detection (BFD) according to some aspects.

FIG. 3 is a ladder diagram 300 illustrating an example of performing BFD according to some aspects. The ladder diagram 300 shows operations performed by the UE 115 and a wireless communication device 302. In some implementations, the wireless communication device 302 includes or corresponds to another UE, and the UE 115 and the wireless communication device 302 communicate via sidelink (SL) communications. In some other implementations, the wireless communication device 302 includes or corresponds to a base station, such as the base station 105 of FIGS. 1 and 2, and the UE 115 and the wireless communication device 302 communicate via DL communications and UL communications.

The wireless communication device 302 periodically transmits BFD RSs to the UE 115, at 310. For example, the wireless communication device 302 may be configured to periodically transmit BFD RSs to the UE 115 (and to other UEs), such as transmitting the BFD RS at a first time, a second time, and an ith time (where i is any integer). If the wireless communication device 302 communicates with the UE 115 using a single transmit (TX) beam, the wireless communication device 302 transmits the BFD RS on the single TX beam. Alternatively, if the wireless communication device 302 communicates with the UE 115 on multiple TX beams, the wireless communication device 302 may transmit the BFD RSs on some or all of the multiple TX beams.

The UE 115 receives the BFD RSs and maintains a count of BFD RSs that are received with a signal strength, such as a layer-1 reference signal received power (L1-RSRP), that satisfies a first threshold, at 312. For example, the UE 115 may measure a signal strength associated with each BFD RS and may count the number of "strong" BFD RSs that are associated with a signal strength that satisfies the first threshold. The count may be maintained for a particular time period. In some implementations, the first threshold and a duration of the particular time period are indicated by messaging from a network entity to the UE 115. In some other implementations, the first threshold and the duration of the particular time period may be preprogrammed at the UE 115. If the UE 115 receives messages and signals from the wireless communication device 302 on a single receive (RX) beam, the UE 115 receives the BFD RS on the single RX beam. Alternatively, if the UE 115 receives messages and signals from the wireless communication device 302 on multiple RX beams, the UE 115 may receive the BFD RSs on some or all of the multiple RX beams. In such implementations, the UE 115 may maintain a count of received BFD RSs that satisfy the first threshold for each beam.

The UE 115 may compare the count of received BFD RSs to a second threshold, at 314. The second threshold may indicate the minimum number of "strong" BFD RSs to be received during the particular time period in order to continue to use a respective beam for communicating with the wireless communication device 302. In some implementations, the second threshold is indicated by messaging from a network entity to the UE 115. In some other implementations, the second threshold may be preprogrammed at the UE 115.

The UE 115 may detect a beam failure for a beam used to receive the BFD RSs if the comparison fails, at 316. For example, if the count of received BFD RSs on a particular beam for the particular time period fails to satisfy the second threshold, the UE 115 may detect beam failure for the particular beam. Beam failure may not indicate complete failure of the beam, instead beam failure may indicate that the beam does not provide sufficient signal strength to continue using for communications with the wireless communication device 302.

Figure 4:
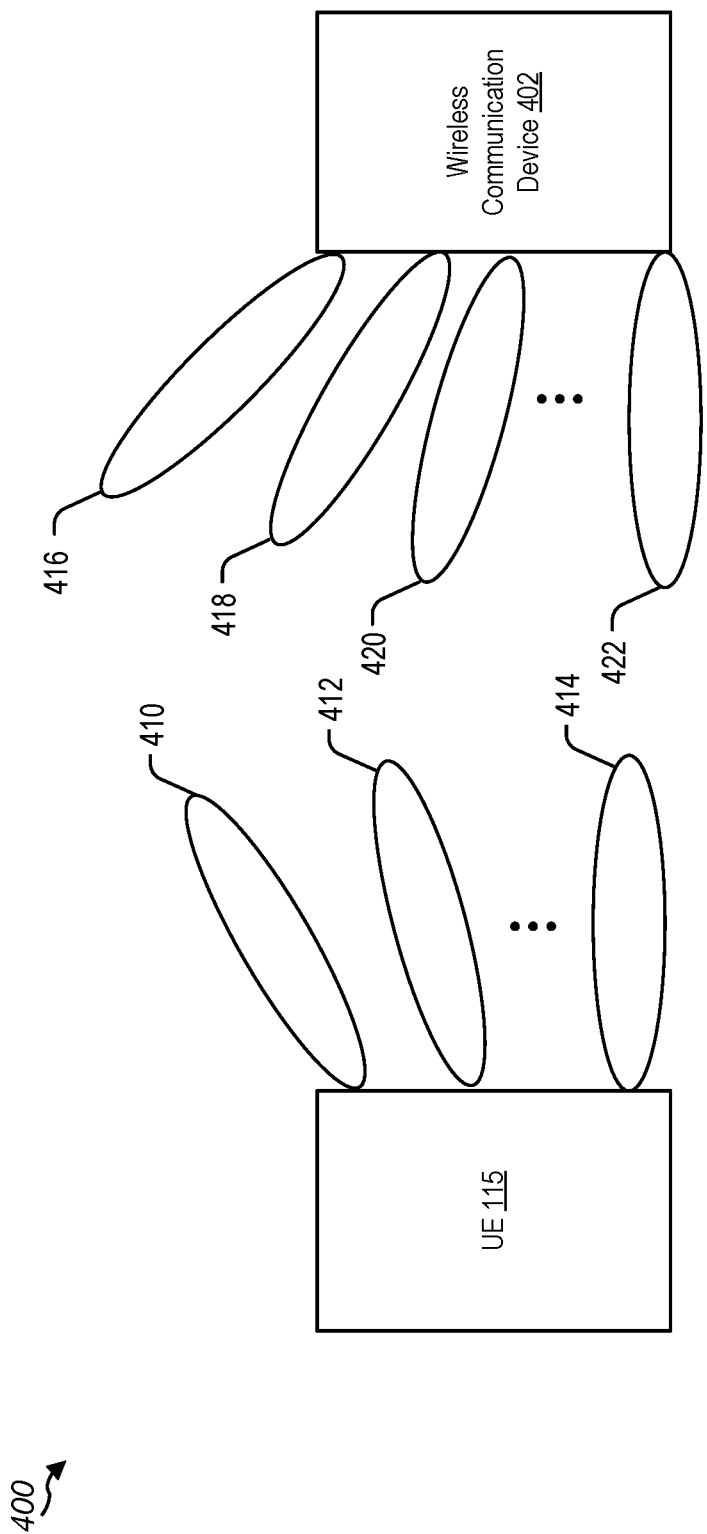
FIG. 4 is a block diagram illustrating an example wireless communication system that supports beam failure recovery (BFR) according to some aspects.

FIG. 4 is a block diagram illustrating an example wireless communication system 400 that supports BFR according to some aspects. BFR may include switching one or more communication beams based on detection of beam failure. For example, the BFR described with reference to the wireless communication system 400 may be performed based on the BFD detection described with reference to FIG. 3.

The wireless communication system 400 includes the UE 115 and a wireless communication device 402. In some implementations, the wireless communication device 402 includes or corresponds to another UE, and the UE 115 and the wireless communication device 402 communicate via SL communications. In some other implementations, the wireless communication device 402 includes or corresponds to a base station, such as the base station 105 of FIGS. 1 and 2, and the UE 115 and the wireless communication device 402 communicate via DL communications and UL communications.

To enable BFR, the wireless communication device 402 may periodically transmit BFR RSs on multiple beams (TX beams), and the UE 115 may perform a beam sweep to receive the BFR RSs on multiple beams (RX beams). For example, as shown in FIG. 4, the wireless communication device 402 may transmit the BFR RSs on a first beam 416, a second beam 418, a third beam 420, and an Mth beam 422 (where M is any positive integer), and the UE 115 may receive the BFR RSs on a first beam 410, a second beam 412, and an Nth beam 414 (where N is any positive integer). N and M may have the same value, or different values, such that the UE 115 and the wireless communication device 402 receive and transmit, respectively, using the same number of beams or a different number of beams. The number of beams, also referred to as antenna beams, supported by each device may be based on antenna arrays (or antenna panels) of the respective devices. For example, the UE 115 may include an antenna array that is configured to generate three beams, and the wireless communication device 402 may include an antenna array that is configured to generate four beams. Although the UE 115 is shown as using three beams, and the wireless communication device 402 is shown as using four beams, in other implementations, the UE 115 may use fewer than three or more than three beams, and the wireless communication device 402 may use fewer than four or more than four beams.

The UE 115 may try to receive the BFR RSs using beams 410-412 and determine a strongest beam. For example, the UE 115 may measure the signal to noise ratio (SNR) associated with each of the beams 410-412 and determine the strongest beam based on the best associated SNR. Based on determining the strongest beam, the UE 115 may transmit an indicator of the strongest beam, and the respective BFR RS transmission, to the wireless communication device 302 to enable the UE 115 and the wireless communication device 402 to use the TX-RX beam pair with the best SNR for future communications. For example, the UE 115 may switch from using a beam that is associated with detection of beam failure to using the strongest beam identified based on the received BFR RSs, and the wireless communication device 402 may switch from using a beam associated with beam failure at the UE 115 to using a beam associated with the best SNR at the UE 115. In some implementations, the indicator of the strongest beam is a random access channel (RACH) preamble that is transmitted by the UE 115 to the wireless communication device 402 in a resource, such as a frequency resource, associated with the BFR RS received on the strongest beam.

In some implementations, the wireless communication device 402 includes or corresponds to a second UE, and the wireless communication device 402 may configure the UE 115 to use a sidelink contention free random access (SL-CFRA) resource for the purpose of BFR. Alternatively, a base station may configure the UE 115 and the wireless communication device 402 (the second UE) to use the SL-CFRA resource for the purpose of BFR. If the SL-CFRA resource is configured for BFR, the wireless communication device 402 periodically transmits a list of BFR RSs, slCandidateBeamRsList. Each BFR RS in slCandidateBeamRsList is transmitted on a respective beam. The beams for the BFR RSs may include one or more beams used to transmit BFD RSs, as described with reference to FIG. 3, or may be different than beams used to transmit the BFD RSs. The BFR RSs in slCandidateBeamRsList may include SL synchronization signal blocks (SL SSBs) or SL channel state information reference signals (SL CSI-RSs). The UE 115 monitors for the BFR RSs in slCandidateBeamRsList. For example, the UE 115 may perform a beam sweep using multiple beams to receive the BFR RSs. The beams used to receive the BFR RSs may be the same or different than the beams used to receive BFD RSs, as described with reference to FIG. 3. If the UE 115 detects a SL SSB or SL CSI-RS in slCandidateBeamRsList with a RSRP that satisfies a threshold ("rsrpThresholdSSB/CSI-RS"), the UE 115 may select the SL SSB or SL CSI-RS with the RSRP greater than the threshold and select a RACH preamble if configured for the selected SL SSB or SL CSI-RS (for a CSI-RS, the UE 115 may back trace to quasi co-location (QCL) SSB). The UE 115 may determine the SL RACH location associated with the selected SSB or CSI-RS to send the RACH preamble to the wireless communication device 402. If a CSI-RS is selected, the UE 115 may use ra-OccasionList or a RACH location corresponding to the SSB (on slCandidateBeamRsList) QCLed with the selected CSI-RS. The UE 115 may initiate a BFR timer when the UE 115 transmits the SL RACH preamble. BFR may be successfully complete with the wireless communication device 402 transmitting to the UE 115 a physical sidelink control channel (PSCCH) scrambled based on a cell radio network temporary identifier (C-RNTI), or some other information, in response to the UE 115 transmitting the SL RACH preamble. In response to receipt of the PSCCH, the UE 115 may stop the BFR timer. Alternatively, if the UE 115 does not receive a PSCCH from the wireless communication device 402 prior to expiration of the BFR timer, the UE 115 may initiate one or more BFR operations with a different resource than the SL-CFRA resource or without the SL-CFRA resource being configured.

In some implementations, the wireless communication device 402 includes or corresponds to a second UE, and the wireless communication device 402 (or a base station) does not configure the UE 115 to use a SL-CFRA resource for the purpose of BFR, or the UE 115 may have detected failure in performing BFR using the SL-CFRA resource. In such implementations, the wireless communication device 402 periodically transmits SL SSBs. The SL SSBs may be transmitted for the purpose of discovery and SL link establishment, such as during an initial sidelink access procedure, and may be transmitted by the wireless communication device 402 using a TX beam sweep. The UE 115 may monitor for the SL SSBs and determine a TX-RX beam pair. For example, the UE 115 may perform a RX beam sweep to receive the SL SSBs. The UE 115 may measure the RSRP associated with each received SL SSB and may select a respective beam and transmit a SL RACH preamble to the wireless communication device 402 using the selected beam in time and frequency resources corresponding to the SL SSB associated with the highest RSRP. The SL RACH preamble may be one of multiple SL RACH preambles, and may be selected based on a grouping. For example, the set of all preambles may be divided into two groups, and the UE 115 may select the SL RACH preamble from a first group to indicate that the respective SL RACH transmission is for the purpose of BFR. The UE 115 may initiate a BFR timer when the UE 115 transmits the SL RACH preamble. BFR may be successfully complete with the wireless communication device 402 transmitting to the UE 115 a PSCCH scrambled based on a C-RNTI, or some other information, in response to the UE 115 transmitting the SL RACH preamble. In response to receipt of the PSCCH, the UE 115 may stop the BFR timer. Alternatively, if the UE 115 does not receive a PSCCH from the wireless communication device 402 prior to expiration of the BFR timer, the UE 115 may determine a sidelink radio link failure (RLF).

Figure 5:
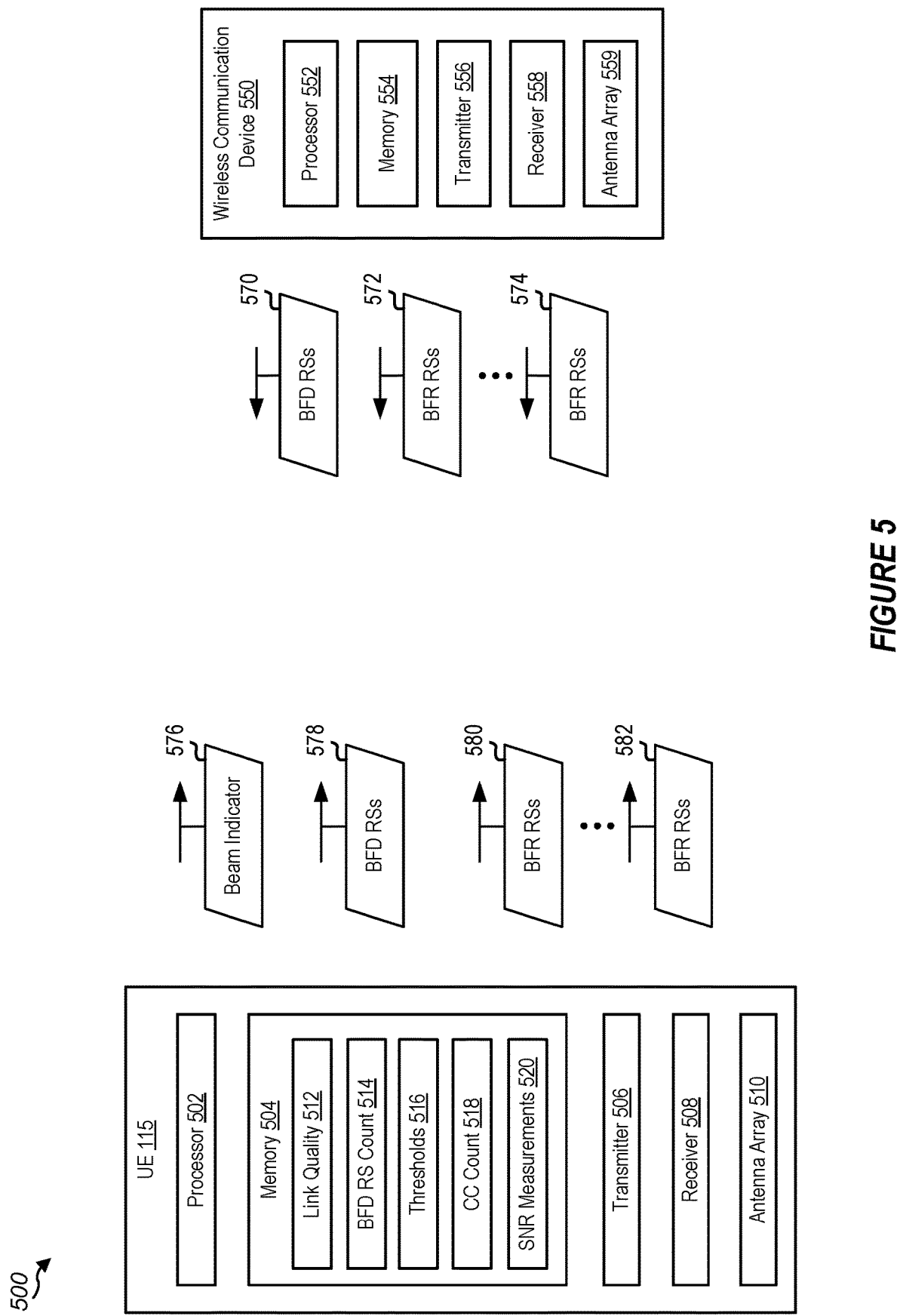
FIG. 5 is a block diagram illustrating an example wireless communication system that supports BFD and BFR with carrier aggregation (CA) according to some aspects of the present disclosure.

FIG. 5 is a block diagram of an example wireless communications system 500 that supports BFD and BFR with CA according to some aspects of the present disclosure. In some examples, the wireless communications system 500 may implement aspects of the wireless network 100. The wireless communications system 500 includes the UE 115 and a wireless communication device 550. Although one UE 115 and one wireless communication device 550 are illustrated, in some other implementations, the wireless communications system 500 may generally include multiple UEs 115, and may include more than one wireless communication device 550 of the same or a different type.

The UE 115 can include a variety of components (such as structural, hardware components) used for carrying out one or more functions described herein. For example, these components can include one or more processors 502 (hereinafter referred to collectively as "the processor 502"), one or more memory devices 504 (hereinafter referred to collectively as "the memory 504"), one or more transmitters 506 (hereinafter referred to collectively as "the transmitter 506"), one or more receivers 508 (hereinafter referred to collectively as "the receiver 508"), and one or more antenna arrays (hereinafter referred to collectively as "the antenna array 510"). The processor 502 may be configured to execute instructions stored in the memory 504 to perform the operations described herein. In some implementations, the processor 502 includes or corresponds to one or more of the receive processor 258, the transmit processor 264, and the controller 280, and the memory 504 includes or corresponds to the memory 282.

In some implementations, the memory 504 may be configured to store a link quality 512, a BFD RS count 514, one or more thresholds 516, a CC count 518, and signal to noise ratio (SNR) measurements 520. The link quality 512 may be a measurement that indicates a quality of a communication link between the UE 115 and the wireless communication device 550 via a particular beam of the UE 115. The BFD RS count 514 may include a count of received BFD RSs during a time period that are associated with signal strengths that satisfy a particular threshold. The threshold 516 may include thresholds used for BFD and BFR, such as a signal strength threshold, a threshold number of BFD RSs, other thresholds, or a combination thereof. The CC count 518 may include a count of CCs supported for wireless communications with the wireless communication device 550 during a time period. The SNR measurements 520 may indicate SNR measurements associated with received BFR RSs at the UE 115.

The transmitter 506 is configured to transmit reference signals, control information and data to one or more other devices, and the receiver 508 is configured to receive references signals, synchronization signals, control information and data from one or more other devices. For example, the transmitter 506 may transmit signaling, control information and data to, and the receiver 508 may receive signaling, control information and data from, the wireless communication device 550. In some implementations, the transmitter 506 and the receiver 508 may be integrated in one or more transceivers. Additionally or alternatively, the transmitter 506 or the receiver 508 may include or correspond to one or more components of the UE 115 described with reference to FIG. 2.

The antenna array 510 may include multiple antenna elements configured to perform wireless communications with other devices, such as with the wireless communication device 550. In some implementations, the antenna array 510 may be configured to perform wireless communications using different beams, also referred to as antenna beams. The beams may include TX beams and RX beams. To illustrate, the antenna array 510 may include multiple independent sets (or subsets) of antenna elements (or multiple individual antenna arrays), and each set of antenna elements of the antenna array 510 may be configured to communicate using a different respective beam that may have a different respective direction than the other beams. For example, a first set of antenna elements of the antenna array 510 may be configured to communicate via a first beam having a first direction, and a second set of antenna elements of the antenna array 510 may be configured to communicate via a second beam having a second direction. In other implementations, the antenna array 510 may be configured to communicate via more than two beams. Alternatively, one or more sets of antenna elements of the antenna array 510 may be configured to concurrently generate multiple beams, for example using multiple radio frequency (RF) chains of the UE 115. Each individual set (or subset) of antenna elements may include multiple antenna elements, such as two antenna elements, four antenna elements, ten antenna elements, twenty antenna elements, or any other number of antenna elements greater than two. Although described as an antenna array, in other implementations, the antenna array 510 may include or correspond to multiple antenna panels, and each antenna panel may be configured to communicate using a different respective beam.

The wireless communication device 550 can include a variety of components (such as structural, hardware components) used for carrying out one or more functions described herein. For example, these components can include one or more processors 552 (hereinafter referred to collectively as "the processor 552"), one or more memory devices 554 (hereinafter referred to collectively as "the memory 554"), one or more transmitters 556 (hereinafter referred to collectively as "the transmitter 556"), one or more receivers 558 (hereinafter referred to collectively as "the receiver 558"), and one or more antenna arrays (hereinafter referred to collectively as "the antenna array 559"). The processor 552 may be configured to execute instructions stored in the memory 554 to perform the operations described herein. In some implementations, the processor 552 includes or corresponds to one or more of the receive processor 238, the transmit processor 220, and the controller 240, and the memory 554 includes or corresponds to the memory 242. Alternatively, the processor 552 may include or correspond to one or more of the receive processor 258, the transmit processor 264, and the controller 280, and the memory 554 may include or correspond to the memory 282.

The transmitter 556 is configured to transmit reference signals, synchronization signals, control information and data to one or more other devices, and the receiver 558 is configured to receive reference signals, control information and data from one or more other devices. For example, the transmitter 556 may transmit signaling, control information and data to, and the receiver 558 may receive signaling, control information and data from, the UE 115. In some implementations, the transmitter 556 and the receiver 558 may be integrated in one or more transceivers. Additionally or alternatively, the transmitter 556 or the receiver 558 may include or correspond to one or more components of base station 105 described with reference to FIG. 2.

The antenna array 559 may include multiple antenna elements configured to perform wireless communications with other devices, such as with the UE 115. In some implementations, the antenna array 559 may be configured to perform wireless communications using different beams, also referred to as antenna beams. The beams may include TX beams and RX beams. To illustrate, the antenna array 559 may include multiple independent sets (or subsets) of antenna elements (or multiple individual antenna arrays), and each set of antenna elements of the antenna array 559 may be configured to communicate using a different respective beam that may have a different respective direction than the other beams. For example, a first set of antenna elements of the antenna array 559 may be configured to communicate via a first beam having a first direction, and a second set of antenna elements of the antenna array 559 may be configured to communicate via a second beam having a second direction. In other implementations, the antenna array 559 may be configured to communicate via more than two beams. Alternatively, one or more sets of antenna elements of the antenna array 559 may be configured to concurrently generate multiple beams, for example using multiple RF chains of the wireless communication device 550. Each individual set (or subset) of antenna elements may include multiple antenna elements, such as two antenna elements, four antenna elements, ten antenna elements, twenty antenna elements, or any other number of antenna elements greater than two. Although described as an antenna array, in other implementations, the antenna array 559 may include or correspond to multiple antenna panels, and each antenna panel may be configured to communicate using a different respective beam.

In some implementations, the wireless communication device 550 may include or correspond to a second UE 115. In such implementations, the UE 115 and the wireless communication device 550 may be configured to communicate using one or more sidelink (SL) communications. In some other implementations, the wireless communication device 550 may include or correspond to a base station, such as the base station 105 of FIGS. 1 and 2. In such implementations, the wireless communication device 550 may be configured to transmit one or more DL communications to the UE 115, and the UE 115 may be configured to transmit one or more UL communications to the wireless communication device 550.

In some implementations, the wireless communications system 500 implements a 5G NR network. For example, the wireless communications system 500 may include multiple 5G-capable UEs 115 and multiple 5G-capable base stations 105, such as UEs and base stations configured to operate in accordance with a 5G NR network protocol such as that defined by the 3GPP. In some implementations, the wireless communications system 500 is configured to support wireless communications, such as between the UE 115 and the wireless communication device 550, in the mmWave band or other high frequencies. Such communications may be performed using narrower, directional beams as compared to communications in the Sub-6 GHz band. In some such implementations, the wireless communications system 500 is configured to support CA in the mmWave band or other high frequencies. For example, the UE 115 and the wireless communication device 550 may communicate via multiple CCs within the mmWave band.

During operation of the wireless communications system 500, the UE 115 and the wireless communication device 550 may communicate using CA. For example, the UE 115 and the wireless communication device 550 may be configured to communicate via multiple (two or more) CCs. Some or all of the multiple CCs may be within the same group of CCs. In some implementations, the group of CCs may be all, or a subset, of the CCs within a particular frequency band. For example, some or all of the multiple CCs may be within the range of approximately 24.25 GHz to 52.6 GHz, such as being within FR2, the mmWave band, or other high frequency bands, as non-limiting examples. In other implementations, the group of CCs may include CCs that span multiple frequency bands. As a non-limiting example, one or more of the multiple CCs may be within another frequency band, such as a sub-6 GHz band.

To enable communications between the UE 115 and the wireless communication device 550, the UE 115 and the wireless communication device 550 may form a communication link. Forming the communication link may include determining multiple beam pairs for wireless communications via the multiple CCs. For example, the UE 115 may determine multiple respective beams for wireless communications with the wireless communication device 550 via the multiple CCs, and the wireless communication device 550 may determine multiple respective beams for wireless communications with the UE 115 via the multiple CCs. To illustrate, the UE 115 may determine N beams for wireless communications (where N is any positive integer), and the wireless communication device 550 may determine M beams for wireless communications (where M is any positive integer). In some examples, the UE may determine N beams for each CC of the multiple CCs such that the respective N beams for a given CC are specific to the CC. In some other examples, the N beams may be the total number of beams and the N beams may be shared across the multiple CCs. In such an example, each CC of the multiple CCs may be associated with the same set of N beams and may use one or more of the N beams that another CC the multiple CCs uses. Similarly, the M beams may be CC-specific or may be shared across the multiple CCs. In some implementations, M and N may be the same number, such that the UE 115 and the wireless communication device 550 use the same number of beams for wireless communications. In such implementations, each of the N beams may have a one-to-one correspondence with a respective one of the M beams. In some other implementations, M and N are different numbers, such that the UE 115 and the wireless communication device 550 use different numbers of beams for wireless communications such that the beams do not have a one-to-one correspondence.

The determination of beams to be used for wireless communications may be performed by a single device. For example, the wireless communication device 550 may transmit reference signals on multiple beams, and the UE 115 may receive the reference signals on multiple beams, such as by performing a beam sweep. The UE 115 may measure signal strengths associated with each of the received reference signals, and the UE 115 may select any beams associated with signal strengths that satisfy one of the thresholds 516 for use in performing wireless communications with the wireless communication device 550. The UE 115 may transmit indicators to the wireless communication device 550 that indicate which received reference signals are associated with the selected beams, and the wireless communication device 550 may select the beams associated with the indicated reference signals for performing wireless communications with the UE 115. This process may be performed for each CC of the multiple CCs, such that the UE 115 and the wireless communication device 550 each select one or more beams for each CC for performing wireless communications, such as one or more of the N beams and one or more of the M beams, respectively. In some other implementations, the UE 115 may transmit the reference signals, and the wireless communication device 550 may select the beams, in a similar manner to that described above for the UE 115. In some other implementations, the UE 115 and the wireless communication device 550 may each transmit reference signals via different CCs, and the UE 115 and the wireless communication device 550 may each select beams for some of the CCs based on the reference signals and indicate the selections to the other device, as described above.

The beam determinations for the multiple CCs may be performed during establishment of a communication link between the UE 115 and the wireless communication device 550. For example, if the wireless communication device 550 is a UE, the determinations and selections of the beams at the UE 115 and the wireless communication device 550 may be part of a process of establishing SL communications between the UE 115 and the wireless communication device 550. Alternatively, if the wireless communication device 550 is a base station, the determinations and selections of the beams at the UE 115 and the wireless communication device 550 may be part of a process of establishing DL communications, UL communications, or both, between the UE 115 and the wireless communication device 550.

To enable BFD, at least one of the UE 115 and the wireless communication device 550 may transmit BFD RSs. For example, the wireless communication device 550 may periodically transmit BFD RSs 570 on one or more TX beams for one or more CCs. The UE 115 may receive the BFD RSs 570 on one or more RX beams for the one or more CCs based on initiation of a BFD process at the UE 115. As an example, the UE 115 may receive the BFD RSs on a first beam for the first CC. The BFD process may be performed periodically, or may be performed based on a triggering event, such as detection of a threshold number of errors in decoded messages or some other triggering event.

As part of the BFD process, the UE 115 may determine the link quality 512 associated with the first beam for the first CC. The link quality 512 may be based on signal strengths associated with received BFD RSs during a time period on the first beam for the first CC. For example, the UE 115 may measure the signal strengths associated with the received BFD RSs and may maintain the BFD RS count 514 of the BFD RSs received during the time period that are associated with a signal strength that satisfies (is greater than or equal to) a first threshold of the thresholds 516, in a similar manner to that described above with reference to FIG. 3. The first threshold may be a threshold signal strength. In some implementations, the received signal strength may include or correspond to a RSRP measurement of the received BFD RS. After updating the BFD RS count 514, the UE 115 may compare the BFD RS count 514 to a second threshold of the thresholds 516. The second threshold may be a threshold number of BFD RSs received with a signal strength that satisfies the first threshold. If the BFD RS count 514 satisfies the second threshold, the UE 115 may determine that the connection with the wireless communication device 550 using the first beam for the first CC is sufficiently strong that the UE 115 may continue to use the first beam for wireless communications with the wireless communication device 550. However, if the BFD RS count 514 fails to satisfy the second threshold, the UE 115 may detect a beam failure for the first beam for the first CC.

Due to similarities between CCs at high frequencies, such as within the mmWave band, failure of a beam for one CC may be associated with failure of a beam for another CC within the same group of CCs. For example, if two CCs are within the same group of CCs, such as being within the same frequency band, the channel propagation characteristics for the two CCs may be sufficiently similar that channel conditions for one CC may be likely to be substantially similar to channel conditions for the other CC. Thus, based on detection of the beam failure of the first beam for the first CC, the UE 115 may automatically determine beam failures of one or more beams for one or more other CCs within the same group of CCs. For example, the UE 115 may determine that there is a beam failure of a second beam of the multiple beams for a second CC of the multiple CCs based on the detection of the beam failure for the first CC and based on the first CC and the second CC being within the same group of CCs. Beam failures for other CCs within the same group of CCs may be similarly determined, such that the UE 115 is able to automatically determine beam failures in other CCs without receiving BFD RSs on the respective beams for the respective CCs and measuring the signal strength of the BFD RSs. Automatically determining beam failures in this manner may reduce power consumption at the UE 115, as compared to receiving BFD RSs on one or more beams on each of the multiple CCs and measuring signal strengths of the respective beams to determine beam failures for the respective CCs.

In some implementations, the same beams are used for each of the multiple CCs. For example, the first beam for the first CC may be the same as the second beam for the second CC. In some other implementations, different beams are used for different CCs. For example, each of the multiple beams may be for a respective one of the multiple CCs for communication between the UE 115 and the wireless communication device 550.

Although described above as the UE 115 performing the BFD, in other implementations, the wireless communication device 550 may perform BFD. For example, the UE 115 may transmit BFD RSs 578, and the wireless communication device 550 may determine whether or not a beam failure occurs based on a number of received BFD RSs satisfying a threshold. Alternatively, each of the UE 115 and the wireless communication device 550 may transmit BFD RSs and determine BFD. In some implementations, the BFD RSs may be concurrently transmitted by different devices via different CCs. For example, prior to detection of the beam failure at the UE 115, the UE 115 may transmit the BFD RSs 578 to the wireless communication device 550 via the second CC on the second beam during the same time period that the wireless communication device 550 transmits the BFD RSs 570 on a respective beam via the first CC. In such implementations, each CC may be reserved for communications in a particular direction, such as from the UE 115 to the wireless communication device 550, or from the wireless communication device 550 to the UE 115, and two CCs associated with different directions of communications may be referred to as "bi-directional CCs" or a "bi-directional CC pair." In some other implementations, multiple devices may transmit BFD RSs via the same CC. For example, prior to detection of the beam failure at the UE 115, the UE 115 may transmit the BFD RSs 578 to the wireless communication device via the first CC on the first beam during different time periods than the wireless communication device transmits the BFD RSs 570 on a respective beam via the first CC. In such examples, BFD RS reception and BFD RS transmission may be performed via the same CC or CCs according to different schedules.

In some implementations, the devices may change which CC is used for transmitting or receiving the respective BFD RSs. For example, the UE 115 may monitor for the BFD RSs 570 via the first CC on at least the first beam during a first time period. Monitoring for the BFD RSs 570 may enable detection of the beam failure of the first beam for the first CC, as described above. Additionally, the UE 115 may switch from receiving the BFD RSs 570 via the first CC on at least the first beam to transmitting the BFD RSs 578 via the first CC on one or more other beams during a second time period that is subsequent to the first time period. The switch from monitoring for the BFD RSs 570 to transmitting the BFD RSs 578 may be scheduled. For example, the UE 115 may cease the monitoring for the BFD RSs 570 and initiate transmission of the BFD RSs 578 based on a predetermined BFD RS schedule or pattern.

Alternatively, the switch from monitoring for the BFD RSs 570 to transmitting the BFD RSs 578 may be based on a triggering event. As a non-limiting example, the triggering event may be a change in the number of CCs used for performing wireless communications with the wireless communication device 550. For example, the UE 115 may determine the CC count 518 of the number of CCs included in the multiple CCs used for wireless communications at a beginning of the first time period, and the UE 115 may determine a second CC count 518 of the number of CCs included in the multiple CCs used for wireless communications at a beginning of the second time period. The UE 115 may cease monitoring for the BFD RSs 570 and initiate transmission of the BFD RSs 578 based on the second CC count 518 being less than the CC count 518. In this manner, if the number of CCs used for wireless communications between the UE 115 and the wireless communication device 550 is reduced during operation of the wireless communications system 500, the UE 115 may change which CCs are used to transmit or receive BFD RSs. The wireless communication device 550 may perform similar operations in at least some implementations. Additionally or alternatively, although described above as detecting the beam failure of the first beam for the first CC based on received BFD RSs 570 on the first beam for the first CC, in other implementations, the UE 115 may receive the BFD RSs 570 using one or more other beams for one or more other CCs to detect a beam failure, and the UE 115 may determine the beam failure of the first beam for the first CC based on the detection of the beam failure for the one or more other CCs and based on the first CC and the one or more other CCs being within the same group of CCs.

After detecting the beam failure of the first beam for the first CC and determining the beam failure of the second beam for the second CC, the UE 115 may perform one or more BFR operations associated with any one or more of the multiple CCs within the same group of CCs as the first CC and the second CC. Due to similarities between CCs at high frequencies, such as within the mmWave band if the group of CCs includes some or all of the CCs within the mmWave band, beam recovery for one CC indicates beam recovery for one or more other CCs within the same group of CCs. Beam recovery may include identifying a different beam to use for wireless communications for a particular CC based on BFR RSs and switching from communicating using the beam associated with beam failure to using the identified beam for performing wireless communications for the particular CC. Such beam switching may be performed for other CCs within the same group of CCs as well, without receiving or performing respective measurements of BFR RSs for the other CCs.

To illustrate, the wireless communication device 550 may periodically transmit multiple BFR RSs, such as a first BFR RS 572 and an Mth BFR RS 574 (where M is any positive integer), on at least two beams for each of one or more CCs. Each BFR RS may be transmitted via a different beam, for one CC or for multiple CCs. For example, the wireless communication device 550 may transmit the first BFR RS 572 on one beam for one CC and the wireless communication device 550 may transmit the Mth BFR RS 574 on another beam for the same CC or another CC. The one or more CCs via which the BFR RSs 572-574 are transmitted are within the same group of CCs as the first CC and the second CC described above, such as the mmWave band. For example, the wireless communication device 550 may transmit the BFR RSs 572-574 on multiple beams, as described with reference to FIG. 4, for each of one or more CCs within the same group of CCs.

In some implementations, the BFR RSs 572-574 may include or correspond to SL SSBs or SL CSI-RSs that are indicated by a BFR RS list. For example, the wireless communication device 550 may include or correspond to a second UE, and the wireless communication device 550 (or a base station) may configure the UE 115 to use a SL-CFRA resource for the purpose of BFR, which may include the wireless communication device transmitting a BFR RS list (slCandidateBeamRsList) to the UE 115, as described above with reference to FIG. 4. Alternatively, the wireless communication device 550 (or the base station) may not configure the UE 115 to use a SL-CFRA resource for the purpose of BFR, and the BFR RSs 572-574 may include or correspond to SL SSBs that are transmitted for the purpose of discovery and SL link establishment. For example, the wireless communication device 550 may transmit the SL SSBs during an initial sidelink access procedure, as described above with reference to FIG. 4. In other implementations, the wireless communication device 550 may include or correspond to a base station, and the BFR RSs 572-574 may include or correspond to other types of messages, such as DL SSBs or DL CSI-RSs, as non-limiting examples.

The UE 115 may monitor for the BFR RSs 572-574 on each of at least two beams for each of the one or more CCs. For example, the UE 115 may monitor for the BFR RSs 572-574 based on detection of the beam failure of the first beam for the first CC. The UE 115 may perform a beam sweep using N beams (where N is any positive integer) to monitor for the BFR RSs 572-574, as described with reference to FIG. 4, for each of the one or more CCs. For example, the UE 115 may perform a beam sweep using the N beams for one of the one or more CCs, followed by performing a respective beam sweep using the N beams for each of the remaining one or more CCs. The UE 115 may receive the BFR RSs 572-574 and may determine metrics associated with the BFR RSs 572-574 on the at least two beams to determine a "strongest" beam of the at least two beams for a respective CC. For example, the UE 115 may determine the SNR measurements 520 associated with the received BFR RSs on the at least two beams, and the UE 115 may identify the strongest beam of the at least two beams that is associated with a highest SNR of the SNR measurements 520 for the respective CC.

The UE 115 may switch from communicating with the wireless communication device 550 on the first beam for the first CC to communicating with the wireless communication device 550 on a third beam for the first CC based on the BFR RSs 572-574. For example, the UE 115 may switch from communicating on the first beam for the first CC to communicating on the third beam for the first CC based on identification of the third beam as being the strongest beam (based on the SNR measurements 520). The UE 115 may also determine to switch beams for communicating with the wireless communication device 550 for one or more other CCs within the same group of CCs based on switching for the first CC. For example, the UE 115 may switch from communicating with the wireless communication device 550 on the second beam for the second CC to communicating with the wireless communication device 550 on a fourth beam for the second CC based on switching from the first beam to the third beam for the first CC and based on the first CC and the second CC being with the same group of CCs. Thus, the UE 115 may perform BFR and determine to switch beams for other CCs without receiving or performing measurements on BFR RSs for the other CCs.

In some implementations, the UE 115 may receive the BFR RSs 572-574 via the same CC as the CC for which the UE 115 detects a beam failure and subsequently performs BFR. For example, the UE 115 may receive the BFR RSs 572-574 via one or more CCs that includes the first CC for which beam failure of the first beam is identified and switching to communicating with the wireless communication device 550 on the third beam is performed. The one or more CCs may alternatively include the second CC, or the one or more CCs may include both the first CC and the second CC. Alternatively, the UE 115 may receive the BFR RSs 572-574 via different CCs than the CC for which the UE 115 detects a beam failure and subsequently performs BFR. For example, the UE 115 may receive the BFR RSs 572-574 via one or more CCs that do not include the first CC for which beam failure is identified and switching to the third beam is performed. Additionally or alternatively, the BFD RSs 570 may be transmitted and received via the same CCs as the BFR RSs 572-574 are transmitted and received. For example, the UE 115 may receive the BFD RSs 570 and the BFR RSs 572-574 via at least the first CC. Alternatively, the BFD RSs 570 and the BFR RSs 572-574 may be transmitted and received via different CCs. For example, the UE 115 may receive the BFD RSs 570 via the first CC, and the UE 115 may receive the BFR RSs 572-574 via one or more other CCs within the same group of CCs as the first CC.

After determining to switch from the first beam to the third beam for the first CC, the UE 115 may transmit a beam indicator 576 to the wireless communication device 550. The beam indicator 576 may indicate a particular BFR RS associated with the strongest beam identified at the UE 115. Receipt of the beam indicator 576 may enable the wireless communication device 550 to switch communication beams. For example, the wireless communication device 550 may switch from communicating with the UE 115 on one beam for the first CC to communicating with the UE 115 on the particular beam associated with the BFR RS indicated by the beam indicator 576 for the first CC. The wireless communication device 550 may also switch beams for communicating via one or more other CCs within the same group of CCs based on switching beams for the first CC, in a similar manner to that described above for the UE 115.

In some implementations, the beam indicator 576 includes or corresponds to a RACH preamble that is transmitted by the UE 115 in a resource or resources, such as time or frequency resources, associated with the received BFR RS that is used to identify the strongest beam. The wireless communication device 550 may receive the RACH preamble and may identify the particular beam used to transmit the BFR RS associated with the resources in which the RACH preamble is received, such that the wireless communication device 550 may switch to communicating with the UE 115 on the particular beam for the first CC. In some implementations, the UE 115 may transmit the RACH preamble and the wireless communication device 550 may transmit the BFR RSs 572-574 via the same CC or CCs. For example, the wireless communication device 550 may transmit the BFR RSs 572-574 via at least the first CC, the second CC, or both, and the UE 115 may transmit the RACH preamble via at least the first CC, the second CC, or both. Alternatively, the UE 115 may transmit the RACH preamble via a different CC or CCs than the CC or CCs used by the wireless communication device 550 to transmit the BFR RSs 572-574. For example, the wireless communication device 550 may transmit the BFR RSs 572-574 via at least the first CC, the second CC, or both, as described above, and the UE 115 may transmit the RACH preamble via another CC that is within the same group of CCs as the first CC and the second CC.

In some other implementations, the beam indicator 576 includes or corresponds to a medium access control (MAC) control element (MAC-CE) message. The MAC-CE message may indicate the BFR RS associated with the strongest beam identified at the UE 115. The UE 115 may transmit the MAC-CE message to the wireless communication device 550 the same CC as the wireless communication device 550 transmits the BFR RSs 572-574, such as at least the first CC, the second CC, or both. In some implementations, the UE 115 may transmit the MAC-CE message via a CC that is not within the same group of CCs as the first CC and the second CC. For example, the first CC and the second CC may be included in a group of CCs within the mmWave band, and the UE 115 may transmit the MAC-CE message via a different CC that is within a sub-6 GHz band, as a non-limiting example.

Although described above as the UE 115 performing the BFR, in other implementations, the wireless communication device 550 may perform BFR. For example, the UE 115 may transmit BFR RSs on at least two beams for the first CC, or multiple CCs including the first CC, and the wireless communication device 550 may determine a beam to be switched to for communicating with the UE 115 via the first CC based on the BFR RSs. For example, the UE 115 may transmit BFR RSs including a first BFR RS 580 and an Nth BFR RS 582 (where N is any positive integer) on respective beams for the first CC, and the wireless communication device 550 may measure SNRs associated with the BFR RSs 580-582 to identify a strongest beam for the first CC at the wireless communication device 550. The BFR RSs 580-582 may include or correspond to SL SSBs or SL CSI-RSs, as non-limiting examples. The wireless communication device 550 may then switch to communicating with the UE 115 on the strongest beam for the first CC. Alternatively, each of the UE 115 and the wireless communication device 550 may transmit BFR RSs and perform BFR. In some implementations, the BFR RSs may be concurrently transmitted by different devices via different CCs. For example, the wireless communication device 550 may periodically transmit the BFR RSs 572-574 on multiple beams for at least the first CC, the second CC, or both, and the UE 115 may periodically transmit the BFR RSs 580-582 to the wireless communication device 550 on multiple beams for one or more other CCs within the same group of CCs as the first CC and the second CC during the same time period. In some other implementations, the BFR RSs may be transmitted by different devices via the same CC or CCs. For example, the wireless communication device 550 may periodically transmit the BFR RSs 572 on multiple beams for at least the first CC, the second CC, or both, and the UE 115 may periodically transmit the BFR RSs 580-582 on multiple beams for at least the first CC, the second CC, or both at different times.

In some implementations, the devices may change which CC is used for transmitting or receiving the respective BFR RSs. For example, the UE 115 may monitor for the BFR RSs 572-574 via at least the first CC on at least the first beam during a first time period. Additionally, the UE 115 may switch from receiving the BFR RSs 572-574 via at least the first CC to transmitting the BFR RSs 580-582 via at least the first CC during a second time period that is subsequent to the first time period. The switch from monitoring for the BFR RSs 572-574 to transmitting the BFR RSs 582-584 may be scheduled or based on a triggering event, as described above with respect to BFD RSs. The wireless communication device 550 may perform similar operations, such as changing from transmitting the BFR RSs 572-574 via at least the first CC during the first time period to monitoring for the BFR RSs 580-582 via at least the first CC during the second time period, in at least some implementations. Alternatively, the BFR RSs 572-574 and the BFR RSs 580-582 may be transmitted via different CCs during each time period, instead of either the BFR RSs 572-574 or the BFR RSs 580-582 being transmitted during each time period.

As described with reference to FIG. 5, the present disclosure provides techniques for BFD and BFR for wireless communications systems that support CA in higher frequency bands, such as the mmWave band, that reduce power consumption at wireless communication devices. For example, the UE 115 and the wireless communication device 550 may be configured to perform wireless communications using multiple CCs within the same group of CCs, such as a group of CCs within the mmWave band. Due to similarities between the CCs at higher frequencies, BFD and BFR may be performed for one CC based on reference signals and, based on performance of the BFD and the BFR, BFD and BFR may be automatically performed for other CCs within the same group of CCs. For example, the UE 115 may detect a beam failure of a first beam for a first CC based on the BFD RSs 570, and the UE 115 may determine a beam failure of a second beam for a second CC based on the determination of the beam failure for the first CC and based on the first CC and the second CC being within the same group of CCs. The UE 115 also may determine to switch from communicating with the wireless communication device 550 on the first beam for the first CC to communicating with the wireless communication device 550 on a third beam for the first CC based on detecting the beam failure of the first beam for the first CC, and the UE 115 may switch from communicating with the wireless communication device 550 on the second beam for the second CC to communicating with the wireless communication device 550 on a fourth beam for the second CC based on the switching for the first CC and based on the first CC and the second CC being within the same group of CCs. Thus, based on performing the BFD and BFR for one CC, the UE 115 and the wireless communication device 550 may perform BFD and BFR for other CCs in the same group of CCs without requiring the reception of, or the performance of measurement on, respective reference signals in the other CCs, which reduces power consumption at the UE 115 and the wireless communication device 550 as compared to receiving respective reference signals via each CC and performing signal measurements on the reference signals in each CC to perform BFD and BFR for each CC. Such reduction in power consumption may be especially advantageous for UEs that communicate via multiple CCs in higher frequency bands using SL communications to perform BFD and BFR over the SL.

FIG. 6 is a flow diagram illustrating an example process 600 that supports BFD for one CC based on BFD for another CC within the same group of CCs according to some aspects. Operations of the process 600 may be performed by a UE, such as the UE 115 described above with reference to FIGS. 1-5 or a UE described with reference to FIG. 8. For example, example operations (also referred to as "blocks") of the process 600 may enable the UE 115 to determine BFD for one CC based on BFD for another CC within the same group of CCs, such as a group of CCs within the mmWave band or other high frequencies, or a group of CCs that spans multiple such frequency bands.

In block 602, the UE 115 determines a plurality of beams for wireless communications with a second wireless communication device via a plurality of CCs. At least a first CC and a second CC of the plurality of CCs are within a same group of CCs. For example, the UE 115 may determine a plurality of beams generated by the antenna array 510 for wireless communications with the wireless communication device 550. In block 604, the UE 115 determines a link quality associated with a first beam of the plurality of beams for the first CC. For example, the UE 115 may determine the link quality 512 based on receipt of the BFD RSs 570 on the first beam for the first CC.

In block 606, the UE 115 detects a beam failure of the first beam for the first CC based on the link quality associated with the first beam for the first CC. For example, the UE 115 may determine a beam failure of the first beam for the first CC based on the link quality 512. In block 608, the UE 115 determines a beam failure of a second beam of the plurality of beams for the second CC based on the detection of the beam failure for the first CC and based on the first CC and the second CC being within the same group of CCs. For example, the UE 115 may determine a beam failure of a second beam for a second CC based on the detected beam failure of the first beam for the first CC and based on the first CC and the second CC being within the same group of CCs.

In some implementations, the first beam for the first CC is the same as the second beam for the second CC. In some other implementations, each of the plurality of beams is for a respective one of the plurality of CCs for communication between the UE and the second wireless communication device. Additionally or alternatively, the same group of CCs may be included in a frequency band within the range of approximately 24.25 GHz to approximately 52.6 GHz, such as FR2 or the mmWave band. The group of CCs may include some or all of the CCs within the frequency band. Alternatively, the group of CCs may include CCs spanning multiple frequency bands. Additionally or alternatively, the second wireless communication device may include a second UE, and the plurality of beams may be for sidelink communications between the UE and the second UE.

In some implementations, determining the link quality associated with the first beam for the first CC includes receiving BFD RSs from the second wireless communication device via the first CC on the first beam and determining a number of the received BFD RSs during a time period that are associated with a signal strength that satisfies a first threshold. For example, the UE 115 may receive the BFD RSs 570 from the wireless communication device 550 and determine the BFD RS count 514 based on the BFD RSs 570 that are associated with a signal strength that satisfies a first threshold of the thresholds 516. In some such implementations, detecting the beam failure of the first beam for the first CC based on the link quality includes detecting the beam failure of the first beam for the first CC based on the determined number of received BFD RSs failing to satisfy a second threshold during the time period. For example, the UE 115 may detect the beam failure of the first beam for the first CC based on the BFD RS count 514 failing to satisfy a second threshold of the thresholds 516 for a time period. In some such implementations, the process 60 may further include transmitting BFD RSs to the second wireless communication device via the second CC on the second beam during the time period, via one or more beams for the first CC during another time period, or a combination thereof. For example, the UE 115 may transmit the BFD RSs 578 to the wireless communication device 550 via the second CC on the second beam during the time period, via one or more beams for the first CC during another time period, via one or more beams for one or more other CCs within the same group of CCs as the first CC and the second CC, or a combination thereof.

In some implementations, the process 600 may include initiating one or more beam failure recovery operations associated with any one or more of the plurality of CCs within the same group of CCs as the first CC and the second CC based on the detection of the beam failure of the first beam for the first CC, the determination of the beam failure of the second beam for the second CC, or both.

In some implementations, the process 600 also includes monitoring for BFD RSs from the second wireless communication device via the first CC on at least the first beam during a first time period, and transmitting BFD RSs to the second wireless communication device via the first CC on one or more other beams during a second time period that is subsequent to the first time period. Detecting the beam failure of the first beam for the first CC is based on the monitoring. For example, the UE 115 may monitor for the BFD RSs 570 via the first CC on at least the first beam during a first time period, and the UE 115 may transmit the BFD RSs 578 via the first CC on one or more other beams during a second time period. In some such implementations, the first time period and the second time period may be based on a predetermined BFR RS schedule, and the process 600 may further include ceasing the monitoring for the BFD RSs before a start of the second time period and initiating the transmission of the BFD RSs during the second time period based on the predetermined BFD RS schedule. Alternatively, the process 600 may further include determining a first number of CCs included in the plurality of CCs at a beginning of the first time period, determining a second number of CCs included in the plurality of CCs at a beginning of the second time period, and ceasing the monitoring for the BFD RSs and initiating the transmission of the BFD RSs based on the second number of CCs being less than the first number of CCs. For example, the UE 115 may determine the CC count 518 of the CCs used for wireless communications at a beginning of the first time period, the UE 115 may determine the second CC count 518 of the CCs used for wireless communications at a beginning of the second time period, and the UE 115 may cease monitoring for the BFD RSs 570 and initiate transmission of the BFD RSs 578 based on the second CC count 518 being less than the CC count 518.

In some implementations, the process 600 may also include receiving BFR RSs from the second wireless communication device on each of at least two beams of the plurality of beams for one or more CCs of the plurality of CCs. The one or more CCs may be within the same group of CCs as the first CC and the second CC, and the at least two beams may include a third beam and a fourth beam of the plurality of beams. For example, the UE 115 may receive the BFR RSs 572-574 from the wireless communication device 550 on each of at least two beams for one or more CCs. The process 600 may further include switching from communicating with the second wireless communication device on the first beam for the first CC to communicating with the second wireless communication device on the third beam for the first CC based on the BFR RSs, and switching from communicating with the second wireless communication device on the second beam for the second CC to communicating with the second wireless communication device on the fourth beam for the second CC based on switching from the first beam to the third beam for the first CC and based on the first CC and the second CC being within the same group of CCs. In some such implementations, the process 600 also includes monitoring for the BFR RSs on each of the at least two beams for the one or more CCs based on the detection of the beam failure of the first beam for the first CC, determining a SNR associated with the BFR RSs received on each of the at least two beams, and identifying a strongest beam of the at least two beams that is associated with a highest SNR. For example, the UE 115 may determine the SNR measurements 520 based on the BFR RSs 572-574 and may identify the strongest beam based on the SNR measurements 520. In some such implementations, the process 600 also includes determining to switch from communicating on the first beam for the first CC to communicating on the third beam for the first CC based on identification of the third beam as being the strongest beam. In some such implementations, the process 600 further includes determining to switch from communicating on the second beam for the second CC to communicating on the fourth beam for the second CC based on identification of the third beam as being the strongest beam.

In some implementations in which the switch from communicating on the first beam for the first CC to communicating on the third beam for the first CC is based on identification of the third beam as the strongest beam, the process 600 may also include transmitting a RACH preamble to the second wireless communication device in a resource associated with the received BFR RS on the third beam based on identification of the third beam as being the strongest beam. For example, the beam indicator 576 may include the RACH preamble. In some such implementations, the RACH preamble may be transmitted via a third CC of the plurality of CCs. The third CC may be within the same group of CCs as the first CC and the second CC. Alternatively, the process 600 may also include transmitting a MAC-CE message to the second wireless communication device via a fourth CC of the plurality of CCs. The MAC-CE message may indicate the received BFR RS on the third beam based on identification of the third beam as being the strongest beam. The fourth CC may be within a different group of CCs than the first CC and the second CC. For example, the beam indicator 576 may include the MAC-CE and may be transmitted via a fourth CC that is not within the same group of CCs as the first CC and the second CC.

In some implementations in which monitoring for the BFR RSs occurs on each of the at least two beams for the one or more CCs based on the detection of the beam failure of the first beam for the first CC, the one or more CCs include the first CC, the second CC, or both. Alternatively, the one or more CCs may be different CCs than the first CC, the second CC, or both. In some such implementations, the process 600 may further include transmitting a RACH preamble to the second wireless communication device via a third CC of the plurality of CCs. The one or more CCs may be different CCs than the third CC. For example, the beam indicator 576 may include the RACH preamble and may be transmitted via a different CC than the CCs via which the BFR RSs 572-574 are transmitted.

FIG. 7 is a flow diagram illustrating an example process 700 that supports BFR for one CC based on BFR for another CC within the same group of CCs according to some aspects. Operations of the process 700 may be performed by a wireless communication device, such as the base station 105 described above with reference to FIGS. 1 and 2, the wireless communication device 550 as described above with reference to FIG. 5, or a wireless communication device as described with reference to FIG. 9. For example, example operations of the process 700 may enable the wireless communication device 550 to perform BFR for one CC based on BFR for another CC within the same group of CCs, such as the mmWave band or other high frequencies.

In block 702, the wireless communication device 550 determines a plurality of beams for wireless communication with a UE via a plurality of CCs. At least a first CC and a second CC of the plurality of CCs are within a same group of CCs. For example, the wireless communication device 550 may determine multiple beams generated by the antenna array 559 for wireless communications with the UE 115. In block 704, the wireless communication device 550 periodically transmits BFR RSs on at least two beams of the plurality of beams for one or more CCs of the plurality of CCs. The one or more CCs are the same group of CCs as the first CC and the second CC, and the at least two beams include a first beam and a second beam of the plurality of beams. For example, the wireless communication device

550 may transmit the BFR RSs 572 to the UE 115 on at least two beams for one or more CCs.

In block 706, the wireless communication device 550 receives an indicator of the second beam from the UE. For example, the wireless communication device 550 may receive the beam indicator 576 from the UE 115. In block 708, the wireless communication device 550 switches from communicating with the UE on the first beam for the first CC to communicating with the UE on a second beam for the first CC based on the receipt of the indicator. In block 710, the wireless communication device 550 switches from communicating with the UE on a third beam of the plurality of beams for the second CC to communicating with the UE on a fourth beam of the plurality of beams for the second CC based on switching from the first beam to the second beam for the first CC and based on the first CC and the second CC being within the same group of CCs.

In some implementations, the first beam for the first CC is the same as the third beam for the second CC, and the second beam for the first CC is the same as the fourth beam for the second CC. In some other implementations, each of the plurality of beams is for a respective one of the plurality of CCs for communication between the wireless communication device and the UE. Additionally or alternatively, the same group of CCs may be included in a frequency band within the range of approximately 24.25 GHz to approximately 52.6 GHz. The group of CCs may include some or all of the CCs within the frequency band. Alternatively, the group of CCs may include CCs spanning multiple frequency bands. Additionally or alternatively, the wireless communication device may include a second UE, and the plurality of beams may be for sidelink communications between the second UE and the UE.

In some implementations, the process 700 may also include periodically transmitting BFD RSs to the UE on the first beam for the first CC prior to receiving the indicator of the second beam. For example, the wireless communication device 550 may periodically transmit the BFD RSs 570 on the first beam for the first CC prior to receiving the beam indicator 576. In some such implementations, the one or more CCs may include the first CC. For example, the wireless communication device 550 may transmit the BFR RSs 572-574 via at least one same CC as the BFD RSs 570. Alternatively, the one or more CCs may be different CCs than the first CC. For example, the wireless communication device 550 may transmit the BFR RSs 572-574 via different CCs than the BFD RSs 570.

In some implementations, receiving the indicator of the second beam may include receiving a RACH preamble from the UE in a resource associated with the second beam. For example, the beam indicator 576 may include or correspond to a RACH preamble received in time and frequency resources associated with the BFR RS transmit on the second beam. In some such implementations, the RACH preamble may be received via a fifth beam of the plurality of beams for a third CC of the plurality of CCs. The third CC may be within the same group of CCs as the first CC and the second CC. In some such implementations, the one or more CCs may be different CCs than the third CC. For example, the wireless communication device 550 may receive the beam indicator 576 via a different CC than the CCs via which the BFR RSs 572-574 are transmitted.

In some implementations, receiving the indicator of the second beam may include receiving a MAC-CE message from the UE via a fourth CC of the plurality of CCs. The MAC-CE message may indicate the second beam, and the fourth CC may be within a different group of CCs than the first CC and the second CC. For example, the beam indicator 576 may include or correspond to a MAC CE that is received via by the wireless communication device 550 via a CC that is not within the same group of CCs as the first CC and the second CC. As a particular example, the MAC CE may be received via a CC within a sub-6 GHz band, and the first CC and the second CC may be within the mmWave band.

Figure 8:
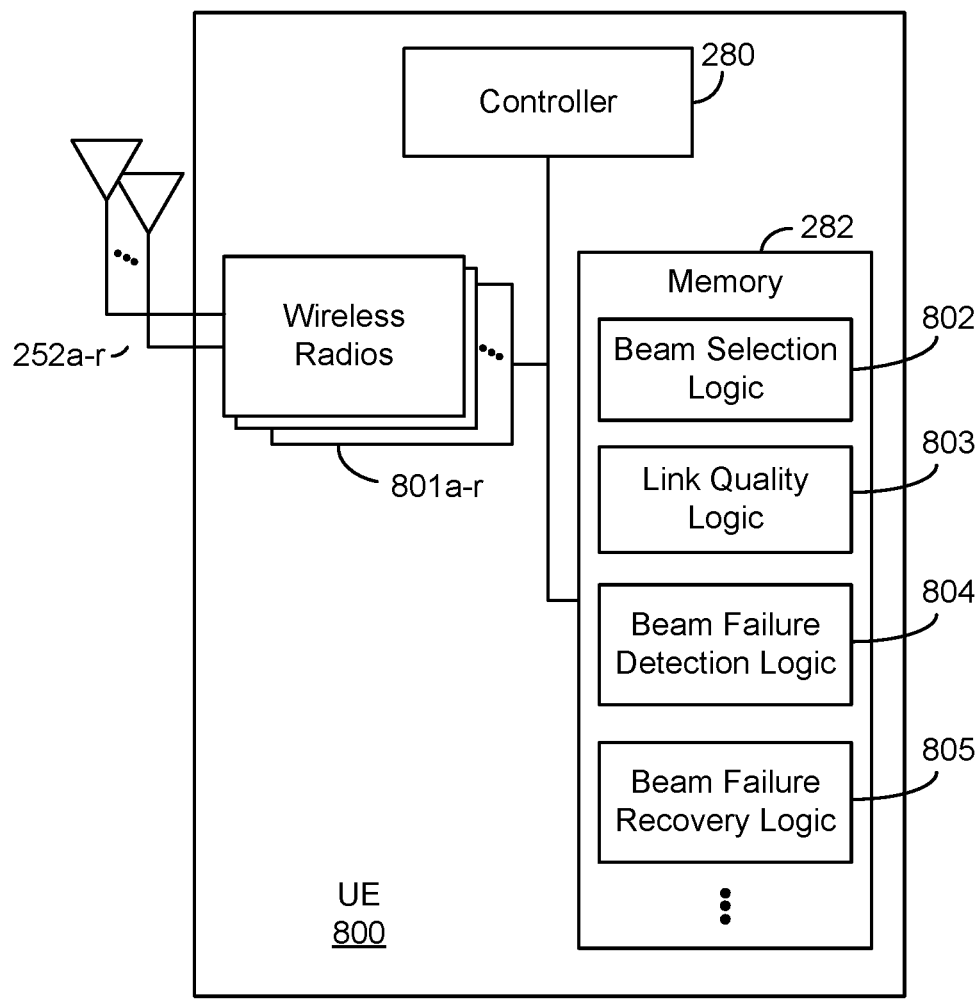
FIG. 8 is a block diagram of an example UE that supports BFD for one CC based on BFD for another CC within the same group of CCs according to some aspects.

FIG. 8 is a block diagram of an example UE 800 that supports BFD for one CC based on BFD for another CC within the same group of CCs according to some aspects. The UE 800 may be configured to perform operations, including the blocks of the process 600 described with reference to FIG. 6, to determine BFD for one CC based on BFD for another CC within the same group of CCs, such as the mmWave band or other high frequencies. In some implementations, the UE 800 includes the structure, hardware, and components shown and described with reference to the UE 115 of FIG. 2 or 5. For example, the UE 800 includes the controller 280, which operates to execute logic or computer instructions stored in the memory 282, as well as controlling the components of the UE 800 that provide the features and functionality of the UE 800. The UE 800, under control of the controller 280, transmits and receives signals via wireless radios 801*a*-*r* and the antennas 252*a*-*r*. The wireless radios 801*a*-*r* include various components and hardware, as illustrated in FIG. 2 for the UE 115, including the modulator and demodulators 254*a*-*r*, the MIMO detector 256, the receive processor 258, the transmit processor 264, and the TX MIMO processor 266.

As shown, the memory 282 may include beam selection logic 802, link quality logic 803, beam failure detection logic 804, and beam failure recovery logic 805. The beam selection logic 802 may be configured to determine multiple beams for multiple CCs for wireless communications with a wireless communication device. The link quality logic 803 may be configured to determine link quality of one or more beams for the multiple CCs based on received BFD RSs. The beam failure detection logic 804 may be configured to detect a first beam failure of a first beam for a first CC based on the link quality associated with the first beam and to determine beam failures for one or more other CCs within the same group of CCs as the first CC based on the detection of the beam failure of the first beam for the first CC and based on the other CCs being within the same group of CCs as the first CC. The beam failure recovery logic 805 may be configured to switch from communicating with the wireless communication device on the first beam for the first CC to communicating with the wireless communication device on a different beam for the first CC based on the detected beam failure of the first beam for the first CC, and to determine to switch from communicating with the wireless communication device via one or more beams for one or more other CCs to communicating with the wireless communication device via one or more different beams for the one or more other CCs based on switching beams for the first CC and based on the one or more other CCs being within the same group of CCs as the first CC. The UE 800 may receive signals from or transmit signals to one or more network entities, such as the base station 105 of FIGS. 1 and 2, the wireless communication device 550 of FIG. 5, another UE, or a wireless communication device as illustrated in FIG. 9.

In some implementations, the UE 800 may be configured to perform the blocks of the process 600 of FIG. 6. To illustrate, the UE 800 may execute, under control of the controller 280, the beam selection logic 802, the link quality logic 803, the beam failure detection logic 804, and the beam failure recovery logic 805 stored in the memory 282. The execution environment of the beam selection logic 802 provides the functionality to perform at least the operations in block 602. The execution environment of the link quality logic 803 provides the functionality to perform at least the operations in block 604. The execution environment of the beam failure detection logic 804 provides the functionality to perform at least the operations in blocks 606 and 608.

Figure 9:
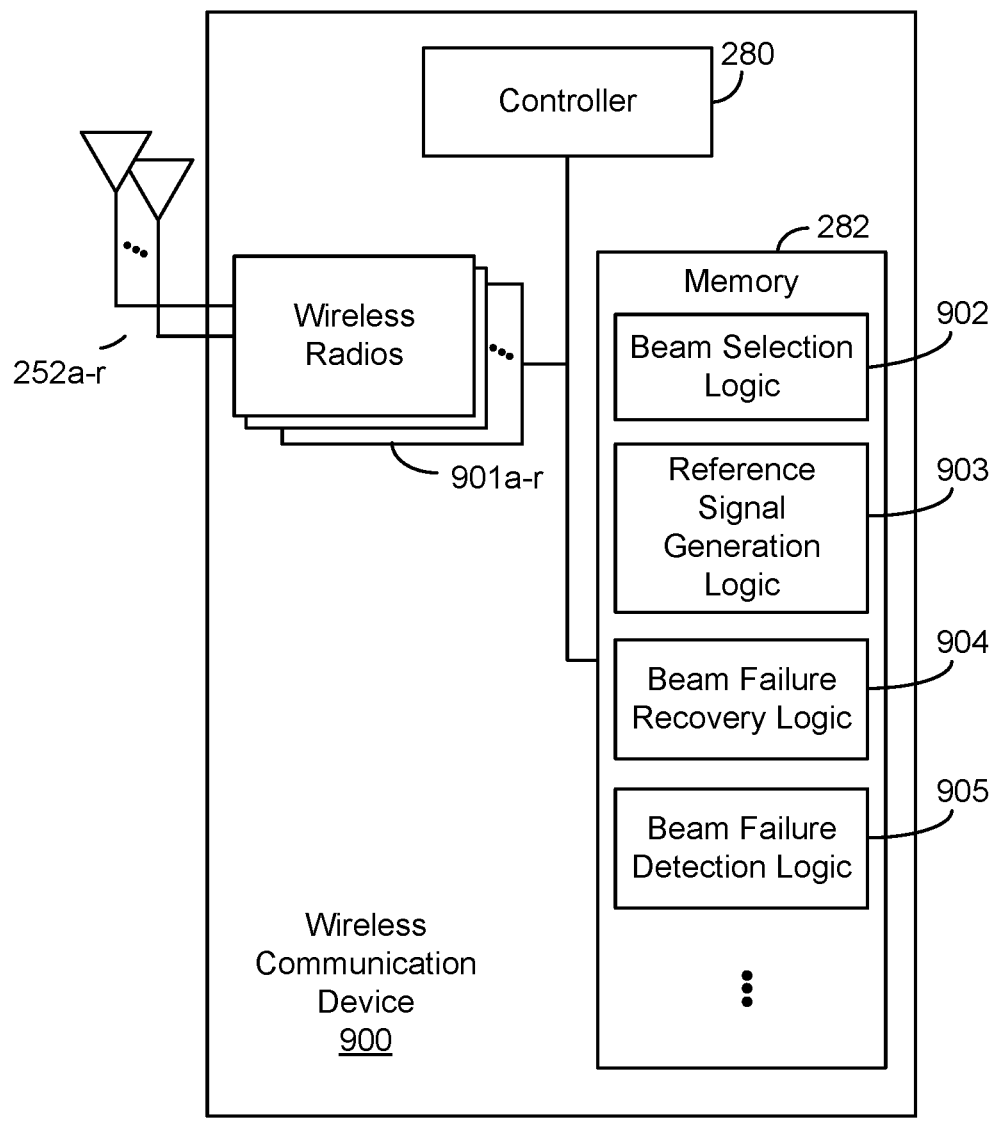
FIG. 9 is a block diagram of an example wireless communication device that supports BFR for one CC based on BFR for another CC within the same group of CCs according to some aspects.

FIG. 9 is a block diagram of an example wireless communication device 900 that supports BFR for one CC based on BFR for another CC within the group of CCs according to some aspects. The wireless communication device 900 may be configured to perform operations, including the blocks of the process described with reference to FIG. 7, to perform BFR for one CC based on BFR for another CC within the same group of CCs, such as CCs within the mmWave band or other high frequencies. In some implementations, the wireless communication device 900 includes the structure, hardware, and components shown and described with reference to the base station 105 of FIGS. 1 and 2, the UE 115 of FIGS. 1-5, or the wireless communication device 550 of FIG. 5. For example, if the wireless communication device 900 includes or corresponds to a UE, the wireless communication device 900 may include the controller 280, which operates to execute logic or computer instructions stored in the memory 282, as well as controlling the components of the wireless communication device 900 that provide the features and functionality of the wireless communication device 900. The wireless communication device 900, under control of the controller 280, transmits and receives signals via wireless radios 901*a-r* and the antennas 252*a-r*. The wireless radios 901*a-r* include various components and hardware, as illustrated in FIG. 2 for the UE 115, including the modulator and demodulators 254*a-r*, the MIMO detector 256, the receive processor 258, the transmit processor 264, and the TX MIMO processor 266. Alternatively, if the wireless communication device 900 includes or corresponds to a base station, the wireless communication device 900 may include components of the base station 105 as described with reference to FIG. 2.

As shown, the memory 282 may include beam selection logic 902, reference signal generation logic 903, beam failure recovery logic 904, and beam failure detection logic 905. The beam selection logic 902 may be configured to determine multiple beams for multiple CCs for wireless communications with a UE. The reference signal generation logic 903 may be configured to generate reference signals, such as BFD RSs and BFR RSs, for periodic transmission. The beam failure recovery logic 904 may be configured to switch from communicating with the UE on a first beam for a first CC to communicating with the UE on a second beam for the first CC based on receipt of a beam indicator from the UE, and to switch from communicating with the UE via one or more beams for one or more other CCs to communicating with the UE via one or more different beams for the one or more other CCs based on switching beams for the first CC and based on the one or more other CCs being within the same group of CCs as the first CC. The beam failure detection logic 905 may be configured to detect a first beam failure of one beam for one CC based on a link quality associated with the one beam and to determine beam failures for one or more other CCs within the same group of CCs as the one CC based on the detection of the beam failure for the first CC and based on the other CCs being within the same group of CCs as the one CC. The wireless communication device 900 may receive signals from or transmit signals to one or more UEs, such as the UE 115 of FIGS. 1-5 or the UE 800 of FIG. 8.

In some implementations, the wireless communication device 900 may be configured to perform the blocks of the process 700 of FIG. 7. To illustrate, the wireless communication device 900 may execute, under control of the controller 280, the beam selection logic 902, the reference signal generation logic 903, the beam failure recovery logic 904, and the beam failure detection logic 905 stored in the memory 282. The execution environment of the beam selection logic 902 provides the functionality to perform at least the operation in block 702. The execution environment of the reference signal generation logic 903 provides the functionality to perform at least the operations in block 704. The wireless radios 901*a-r* and the antennas 252*a-r* provide the functionality to perform at least the operations in block 706. The execution environment of the beam failure recovery logic 904 provides the functionality to perform at least the operations in blocks 708 and 710.

It is noted that one or more blocks (or operations) described with reference to FIGS. 6 and 7 may be combined with one or more blocks (or operations) described with reference to another of the figures. For example, one or more blocks (or operations) of FIG. 6 may be combined with one or more blocks (or operations) of FIG. 7. As another example, one or more blocks associated with FIG. 6 or 7 may be combined with one or more blocks (or operations) associated with FIG. 2 or 5. Additionally, or alternatively, one or more operations described above with reference to FIGS. 1-8 may be combined with one or more operations described with reference to FIG. 9.

In some aspects, techniques for enabling BFD and BFR for one or more CCs based on BFD and BFR for one CC within the same group of CCs may include additional aspects, such as any single aspect or any combination of aspects described below or in connection with one or more other processes or devices described elsewhere herein. In some aspects, enabling BFD for one or more CCs based on BFD for one CC within the same group of CCs may include an apparatus configured to determine a plurality of beams for wireless communications with a second wireless communication device via a plurality of CCs. At least a first CC and a second CC of the plurality of CCs may be within a same group of CCs. The apparatus may also be configured to determine a link quality associated with a first beam of the plurality of beams for the first CC. The apparatus may be configured to detect a beam failure of the first beam for the first CC based on the link quality associated with the first beam for the first CC. The apparatus may further be configured to determine a beam failure of a second beam of the plurality of beams for the second CC based on the detection of the beam failure for the first CC and based on the first CC and the second CC being within the same group of CCs. In some implementations, the apparatus includes a wireless device, such as a UE. In some implementations, the apparatus may include at least one processor, and a memory coupled to the processor. The processor may be configured to perform operations described herein with respect to the wireless device. In some other implementations, the apparatus may include a non-transitory computer-readable medium having program code recorded thereon and the program code may be executable by a computer for causing the computer to perform operations described herein with reference to the wireless device. In some implementations, the apparatus may include one or more means configured to perform operations described herein.

In a first aspect, the first beam for the first CC is the same as the second beam for the second CC.

In a second aspect, each of the plurality of beams is for a respective one of the plurality of CCs for communication between the UE and the second wireless communication device.

In a third aspect, alone or in combination with one or more of the first through second aspects, the same group of CCs are included in a frequency band within the range of approximately 24.25 GHz to approximately 52.6 GHz.

In a fourth aspect, alone or in combination with one or more of the first through third aspects, the second wireless communication device comprises a second UE, and the plurality of beams are for sidelink communications between the UE and the second UE.

In a fifth aspect, alone or in combination with one or more of the first through fourth aspects, wherein determining the link quality associated with the first beam for the first CC comprises receiving BFD RSs from the second wireless communication device via the first CC on the first beam, and determining a number of the received BFD RSs during a time period that are associated with a signal strength that satisfies a first threshold.

In a sixth aspect, in combination with the fifth aspect, detecting the beam failure of the first beam for the first CC based on the link quality comprises detecting the beam failure of the first beam for the first CC based on the determined number of received BFD RSs failing to satisfy a second threshold during the time period.

In a seventh aspect, in combination with one or more of the fifth through sixth aspects, the apparatus transmits BFD RSs to the second wireless communication device via the second CC on the second beam during the time period, via one or more beams for the first CC during another time period, or a combination thereof.

In an eighth aspect, alone or in combination with one or more of the first through seventh aspects, the apparatus initiates one or more beam failure recovery operations associated with any one or more of the plurality of CCs within the same group of CCs as the first CC and the second CC based on the detection of the beam failure of the first beam for the first CC, the determination of the beam failure of the second beam for the second CC, or both.

In a ninth aspect, alone or in combination with one or more of the first through eighth aspects, the apparatus monitors for BFD RSs from the second wireless communication device via the first CC on at least the first beam during a first time period. Detecting the beam failure of the first beam for the first CC is based on the monitoring. The apparatus also transmits BFD RSs to the second wireless communication device via the first CC on one or more other beams during a second time period that is subsequent to the first time period.

In a tenth aspect, in combination with the ninth aspect, the first time period and the second time period are based on a predetermined BFD RS schedule, and the apparatus ceases the monitoring for the BFD RSs before a start of the second time period and initiates the transmission of the BFD RSs during the second time period based on the predetermined BFD RS schedule.

In an eleventh aspect, in combination with one or more of the ninth through tenth aspects, the apparatus determines a first number of CCs included in the plurality of CCs at a beginning of the first time period, determines a second number of CCs included in the plurality of CCs at a beginning of the second time period, and ceases the monitoring for the BFD RSs and initiating the transmission of the BFD RSs based on the second number of CCs being less than the first number of CCs.

In a twelfth aspect, alone or in combination with one or more of the first through eleventh aspects, the apparatus receives BFR RSs from the second wireless communication device on each of at least two beams of the plurality of beams for one or more CCs of the plurality of CCs. The one or more CCs are within the same group of CCs as the first CC and the second CC, and the at least two beams include a third beam and a fourth beam of the plurality of beams. The apparatus also switches from communicating with the second wireless communication device on the first beam for the first CC to communicating with the second wireless communication device on the third beam for the first CC based on the BFR RSs, and switches from communicating with the second wireless communication device on the second beam for the second CC to communicating with the second wireless communication device on the fourth beam for the second CC based on switching from the first beam to the third beam for the first CC and based on the first CC and the second CC being within the same group of CCs.

In a thirteenth aspect, in combination with the twelfth aspect, the apparatus monitors for the BFR RSs on each of the at least two beams for the one or more CCs based on the detection of the beam failure of the first beam for the first CC, determines a SNR associated with the BFR RSs received on each of the at least two beams, and identifies a strongest beam of the at least two beams that is associated with a highest SNR.

In a fourteenth aspect, in combination with the thirteenth aspect, the apparatus determines to switch from communicating on the first beam for the first CC to communicating on the third beam for the first CC based on identification of the third beam as being the strongest beam.

In a fifteenth aspect, in combination with the fourteenth aspect, the apparatus determines to switch from communicating on the second beam for the second CC to communicating on the fourth beam for the second CC based on identification of the third beam as being the strongest beam.

In a sixteenth aspect, in combination with one or more of the fourteenth through fifteenth aspects, the apparatus transmits a RACH preamble to the second wireless communication device in a resource associated with the received BFR RS on the third beam based on identification of the third beam as being the strongest beam.

In a seventeenth aspect, in combination with the sixteenth aspect, the RACH preamble is transmitted via a third CC of the plurality of CCs. The third CC is within the same group of CCs as the first CC and the second CC.

In an eighteenth aspect, alone or in combination with one or more of the fourteenth through fifteenth aspects, the apparatus transmits a MAC-CE message to the second wireless communication device via a fourth CC of the plurality of CCs. The MAC-CE message indicates the received BFR RS on the third beam based on identification of the third beam as being the strongest beam. The fourth CC is within a different group of CCs than the first CC and the second CC.

In a nineteenth aspect, in combination with one or more of the twelfth through eighteenth aspects, the one or more CCs include the first CC, the second CC, or both.

In a twentieth aspect, in combination with one or more of the twelfth through eighteenth aspects, the one or more CCs are different CCs than the first CC, the second CC, or both.

In a twenty-first aspect, in combination with the twentieth aspect, the apparatus transmits a RACH preamble to the second wireless communication device via a third CC of the plurality of CCs. The one or more CCs are different CCs than the third CC.

In some aspects, an apparatus configured for wireless communication, such as a wireless communication device, is configured to determine a plurality of beams for wireless communication with a UE via a plurality of CCs. At least a first CC and a second CC of the plurality of CCs are within a same group of CCs. The apparatus is also configured to periodically transmit BFR RSs on at least two beams of the plurality of beams for one or more CCs of the plurality of CCs. The one or more CCs are within the same group of CCs as the first CC and the second CC, and the at least two beams include a first beam and a second beam of the plurality of beams. The apparatus is configured to receive an indicator of the second beam from the UE. The apparatus is also configured to switch from communicating with the UE on the first beam for the first CC to communicating with the UE on a second beam for the first CC based on the receipt of the indicator. The apparatus is further configured to switch from communicating with the UE on a third beam of the plurality of beams for the second CC to communicating with the UE on a fourth beam of the plurality of beams for the second CC based on switching from the first beam to the second beam for the first CC and based on the first CC and the second CC being within the same group of CCs. In some implementations, the apparatus includes a wireless device, such as a UE or a base station. In some implementations, the apparatus may include at least one processor, and a memory coupled to the processor. The processor may be configured to perform operations described herein with respect to the wireless device. In some other implementations, the apparatus may include a non-transitory computer-readable medium having program code recorded thereon and the program code may be executable by a computer for causing the computer to perform operations described herein with reference to the wireless device. In some implementations, the apparatus may include one or more means configured to perform operations described herein.

In a twenty-second aspect, the first beam for the first CC is the same as the third beam for the second CC, and the second beam for the first CC is the same as the fourth beam for the second CC.

In twenty-third aspect, each of the plurality of beams is for a respective one of the plurality of CCs for communication between the wireless communication device and the UE.

In a twenty-fourth aspect, alone or in combination with one or more of the twenty-second through twenty-third aspects, the same group of CCs are included in a frequency band within the range of approximately 24.25 GHz to approximately 52.6 GHz.

In a twenty-fifth aspect, alone or in combination with one or more of the twenty-second through twenty-fourth aspects, the wireless communication device comprises a second UE, and the plurality of beams are for sidelink communications between the second UE and the UE.

In a twenty-sixth aspect, alone or in combination with one or more of the twenty-second through twenty-fifth aspects, the apparatus periodically transmits BFD RSs to the UE on the first beam for the first CC prior to receiving the indicator of the second beam.

In a twenty-seventh aspect, in combination with the twenty-sixth aspect, the one or more CCs include the first CC.

In a twenty-eighth aspect, in combination with the twenty-sixth aspect, the one or more CCs are different CCs than the first CC.

In a twenty-ninth aspect, alone or in combination with one or more of the twenty-second through twenty-eighth aspects, receiving the indicator of the second beam comprises receiving a RACH preamble from the UE in a resource associated with the second beam.

In a thirtieth aspect, in combination with the twenty-ninth aspect, the RACH preamble is received via a fifth beam of the plurality of beams for a third CC of the plurality of CCs. The third CC is within the same group of CCs as the first CC and the second CC.

In a thirty-first aspect, in combination with the thirtieth aspect, the one or more CCs are different CCs than the third CC.

In a thirty-second aspect, alone or in combination with one or more of the twenty-second through twenty-eighth aspects, receiving the indicator of the second beam comprises receiving a MAC-CE message from the UE via a fourth CC of the plurality of CCs. The MAC-CE message indicates the second beam. The fourth CC is within a different group of CCs than the first CC and the second CC.

In a thirty-third aspect, an apparatus configured for wireless communication, such as a UE, is configured to detect a beam failure of a first beam of a plurality of beams for a first CC of a plurality of CCs based on a link quality associated with the first beam for the first CC. The plurality of beams are for wireless communications with a second wireless communication device via the plurality of CCs. At least the first CC and a second CC of the plurality of CCs are within a same group of CCs. The apparatus is further configured to initiate one or more beam failure recovery operations associated with any one or more of the plurality of CCs within the same group of CCs as the first CC and the second CC based on a determination of a beam failure of a second beam of the plurality of beams for the second CC. The determination is based on the detection of the beam failure for the first CC and based on the first CC and the second CC being within the same group of CCs. In some implementations, the apparatus includes a wireless device, such as a UE or a base station. In some implementations, the apparatus may include at least one processor, and a memory coupled to the processor. The processor may be configured to perform operations described herein with respect to the wireless device. In some other implementations, the apparatus may include a non-transitory computer-readable medium having program code recorded thereon and the program code may be executable by a computer for causing the computer to perform operations described herein with reference to the wireless device. In some implementations, the apparatus may include one or more means configured to perform operations described herein.

In a thirty-fourth aspect, in combination with the thirty-third aspect, the first beam for the first CC is the same as the second beam for the second CC.

In a thirty-fifth aspect, in combination with one or more of the thirty-third aspect or the thirty-fourth aspect, the second wireless communication device includes a second UE. The plurality of beams are for sidelink communications between the apparatus and the second UE.

In a thirty-sixth aspect, in combination with one or more of the thirty-third through thirty-fifth aspects, determining the link quality associated with the first beam for the first CC includes receiving BFD RSs from the second wireless communication device via the first CC on the first beam and determining a number of the received BFD RSs during a time period that are associated with a signal strength that satisfies a first threshold. Detecting the beam failure of the first beam for the first CC based on the link quality includes detecting the beam failure of the first beam for the first CC based on the determined number of received BFD RSs failing to satisfy a second threshold during the time period.

In a thirty-seventh aspect, in combination with the thirty-sixth aspect, the apparatus is further configured to transmit BFD RSs to the second wireless communication device via the second CC on the second beam during the time period, via one or more beams for the first CC during another time period, or a combination thereof.

In a thirty-eighth aspect, in combination with one or more of the thirty-third through thirty-seventh aspects, the apparatus is further configured to monitor for BFD RSs from the second wireless communication device via the first CC on at least the first beam during a first time period. Detecting the beam failure of the first beam for the first CC is based on the monitoring. The apparatus is also configured to transmit BFD RSs to the second wireless communication device via the first CC on one or more other beams during a second time period that is subsequent to the first time period.

In a thirty-ninth aspect, in combination with the thirty-eighth aspect, the apparatus is further configured to cease the monitoring for the BFD RSs and initiate the transmission of the BFD RSs based on a number of CCs included in the plurality of CCs at a beginning of the second time period being less than a number of CCs included in the plurality of CCs at the beginning of the first time period or based on a predetermined BFD RS schedule associated with transmission of the BFD RSs by the second wireless communication device.

In a fortieth aspect, in combination with one or more of the thirty-third through thirty-ninth aspects, the apparatus is further configured to receive BFR RSs from the second wireless communication device on each of at least two beams of the plurality of beams for one or more CCs of the plurality of CCs. The one or more CCs are within the same group of CCs as the first CC and the second CC. The at least two beams include a third beam and a fourth beam of the plurality of beams. The apparatus is also configured to switch from communicating with the second wireless communication device on the first beam for the first CC to communicating with the second wireless communication device on the third beam for the first CC based on the BFR RSs. The apparatus is further configured to switch from communicating with the second wireless communication device on the second beam for the second CC to communicating with the second wireless communication device on the fourth beam for the second CC based on switching from the first beam to the third beam for the first CC and based on the first CC and the second CC being within the same group of CCs.

In a forty-first aspect, in combination with the fortieth aspect, the apparatus is further configured to transmit a RACH preamble to the second wireless communication device in a resource associated with the received BFR RS on the third beam based on identification of the third beam as being a strongest beam of the at least two beams. The RACH preamble is transmitted via a third CC of the plurality of CCs. The third CC is within the same group of CCs as the first CC and the second CC.

In a forty-second aspect, in combination with one or more of the fortieth and forty-first aspects, the apparatus is further configured to transmit a MAC-CE message to the second wireless communication device via a fourth CC of the plurality of CCs. The MAC-CE message indicates the received BFR RS on the third beam based on identification of the third beam as being a strongest beam of the at least two beams. The fourth CC is within a different group of CCs than the first CC and the second CC.

In a forty-third aspect, an apparatus configured for wireless communication, is configured to periodically transmit BFR RSs on at least two beams of a plurality of beams for one or more CCs of a plurality of CCs. The plurality of beams are for wireless communication with a UE via the plurality of CCs. The one or more CCs are within a same group of CCs as a first CC and a second CC of the plurality of CCs. The at least two beams include a first beam and a second beam of the plurality of beams. The apparatus is also configured to receive an indicator of the second beam from the UE. The apparatus is configured to switch from communicating with the UE on the first beam for the first CC to communicating with the UE on a second beam for the first CC based on the receipt of the indicator. The apparatus is further configured to switch from communicating with the UE on a third beam of the plurality of beams for the second CC to communicating with the UE on a fourth beam of the plurality of beams for the second CC based on switching from the first beam to the second beam for the first CC and based on the first CC and the second CC being within the same group of CCs. In some implementations, the apparatus includes a wireless device, such as a UE or a base station. In some implementations, the apparatus may include at least one processor, and a memory coupled to the processor. The processor may be configured to perform operations described herein with respect to the wireless device. In some other implementations, the apparatus may include a non-transitory computer-readable medium having program code recorded thereon and the program code may be executable by a computer for causing the computer to perform operations described herein with reference to the wireless device. In some implementations, the apparatus may include one or more means configured to perform operations described herein.

In a forty-fourth aspect, in combination with the forty-third aspect, the first beam for the first CC is the same as the third beam for the second CC, and the second beam for the first CC is the same as the fourth beam for the second CC.

In a forty-fifth aspect, in combination with one or more of the forty-third or forty-fourth aspects, the apparatus is further configured to periodically transmit BFD RSs to the UE on the first beam for the first CC prior to receiving the indicator of the second beam.

In a forty-sixth aspect, in combination with one or more of the forty-third through forty-fifth aspects, receiving the indicator of the second beam includes receiving a RACH preamble from the UE in a resource associated with the second beam.

In a forty-seventh aspect, in combination with one or more of the forty-third through forty-sixth aspects, receiving the indicator of the second beam includes receiving a MAC-CE message from the UE via a fourth CC of the plurality of CCs. The MAC-CE message indicates the second beam. The fourth CC is within a different group of CCs than the first CC and the second CC.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Components, the functional blocks, and the modules described herein with respect to FIGS. 1-9 include processors, electronics devices, hardware devices, electronics components, logical circuits, memories, software codes, firmware codes, among other examples, or any combination thereof. In addition, features discussed herein may be implemented via specialized processor circuitry, via executable instructions, or combinations thereof.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Skilled artisans will also readily recognize that the order or combination of components, methods, or interactions that are described herein are merely examples and that the components, methods, or interactions of the various aspects of the present disclosure may be combined or performed in ways other than those illustrated and described herein.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. In some implementations, a processor may be implemented as a combination of computing devices, such as a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, that is one or more modules of computer program instructions, encoded on a computer storage media for execution by, or to control the operation of, data processing apparatus.

If implemented in software, the functions may be stored on or transmitted over as one or more instructions or code on a computer-readable medium. The processes of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to some other implementations without departing from the spirit or scope of this disclosure. Thus, the claims are not intended to be limited to the implementations shown herein, but are to be accorded the widest scope consistent with this disclosure, the principles and the novel features disclosed herein.

Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper orientation of any device as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, some other implementations are within the scope of the following claims. In some cases, the actions recited in the claims can be performed in a different order and still achieve desirable results.

As used herein, including in the claims, the term "or," when used in a list of two or more items, means that any one of the listed items can be employed by itself, or any combination of two or more of the listed items can be employed. For example, if a composition is described as containing components A, B, or C, the composition can contain A alone; B alone; C alone; A and B in combination; A and C in combination; B and C in combination; or A, B, and C in combination. Also, as used herein, including in the claims, "or" as used in a list of items prefaced by "at least one of" indicates a disjunctive list such that, for example, a list of "at least one of A, B, or C" means A or B or C or AB or AC or BC or ABC (that is A and B and C) or any of these in any combination thereof. The term "substantially" is defined as largely but not necessarily wholly what is specified (and includes what is specified; for example, substantially 90 degrees includes 90 degrees and substantially parallel includes parallel), as understood by a person of ordinary skill in the art. In any disclosed implementations, the term "substantially" may be substituted with "within [a percentage] of" what is specified, where the percentage includes 0.1, 1, 5, or 10 percent.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. A method for wireless communication performed by a user equipment (UE), the method comprising:
receiving beam failure detection reference signals (BFD RSs) from a second wireless communication device via a first component carrier (CC) of a group of CCs via a first beam of a group of beams, the group of CCs further including a second CC and the group of beams further including a second beam for communication via the second CC;
detecting a beam failure of the first beam for the first CC in accordance with a number of the BFD RSs received during a first time period that have a signal strength that satisfies a threshold;
ceasing monitoring for BFD RSs from the second wireless communication device and initiating transmission of BFD RSs to the second wireless communication device via the first CC on one or more other beams during a second time period that is subsequent to the first time period based on a number of CCs included in the group of CCs at a beginning of the second time period being less than a number of CCs included in the group of CCs at the beginning of the first time period or based on a predetermined BFD RS schedule associated with transmission of the BFD RSs by the second wireless communication device; and
initiating a beam failure recovery operation that selects a new beam for the second CC in accordance with the detection of the beam failure of the first beam for the first CC and in accordance with the first CC and the second CC being both within the group of CCs.

2. The method of claim 1, wherein the first beam for the first CC is the same as the second beam for the second CC.

3. The method of claim 1, wherein the second wireless communication device comprises a second UE, and wherein the group of beams are for sidelink communications between the UE and the second UE.

4. The method of claim 1, further comprising transmitting BFD RSs to the second wireless communication device via the second CC on the second beam during the first time period.

5. The method of claim 1, further comprising:
receiving beam failure recovery reference signals (BFR RSs) from the second wireless communication device via the first CC via a third beam; and
switching from communicating with the second wireless communication device via the first beam for the first CC to communicating with the second wireless communication device via the third beam for the first CC in accordance with the BFR RSs received via the first CC via the third beam; and
wherein the beam failure recovery operation comprises switching from communicating with the second wireless communication device via the second beam for the second CC to communicating with the second wireless communication device via a fourth beam for the second CC in accordance with the BFR RSs received via the first CC via the third beam and in accordance with the first CC and the second CC both being within the group of CCs, wherein the new beam is the fourth beam.

6. The method of claim 5, further comprising transmitting a random access channel (RACH) preamble to the second wireless communication device in a resource associated with the received BFR RS on the third beam in accordance with identification of the third beam as being a strongest beam, wherein the RACH preamble is transmitted via a third CC of the group of CCs.

7. The method of claim 5, further comprising transmitting a medium access control (MAC) control element (MAC-CE) message to the second wireless communication device via a fourth CC, the MAC-CE message indicating the received BFR RS on the third beam in accordance with identification of the third beam as being a strongest beam, wherein the fourth CC is within a different group of CCs than the first CC and the second CC.

8. A user equipment (UE) comprising:
at least one processor; and
a memory coupled with the at least one processor and storing processor-readable code that, when executed by the at least one processor, is configured to:
receive beam failure detection reference signals (BFD RSs) from a second wireless communication device via a first component carrier (CC) of a group of CCs via a first beam of a group of beams, the group of CCs further including a second CC and the group of beams further including a second beam for communication via the second CC;
detect a beam failure of the first beam for the first CC in accordance with a number of the BFD RSs received during a first time period that have a signal strength that satisfies a threshold;

cease monitoring for BFD RSs from the second wireless communication device and initiating transmission of BFD RSs to the second wireless communication device via the first CC on one or more other beams during a second time period that is subsequent to the first time period based on a number of CCs included in the group of CCs at a beginning of the second time period being less than a number of CCs included in the group of CCs at the beginning of the first time period or based on a predetermined BFD RS schedule associated with transmission of the BFD RSs by the second wireless communication device; and initiate a beam failure recovery operation to select a new beam for the second CC in accordance with the detection of the beam failure of the first beam for the first CC and in accordance with the first CC and the second CC being both within the group of CCs.

9. The UE of claim 8, wherein the first beam for the first CC is the same as the second beam for the second CC.

10. The UE of claim 8, wherein the second wireless communication device comprises a second UE, and wherein the group of beams are for sidelink communications between the UE and the second UE.

11. The UE of claim 8, wherein the at least one processor is further configured to transmit BFD RSs to the second wireless communication device via the second CC on the second beam during the first time period.

12. The UE of claim 8, wherein the at least one processor is further configured to:

receive beam failure recovery reference signals (BFR RSs) from the second wireless communication device via the first CC via a third beam; and switch from communicating with the second wireless communication device via the first beam for the first CC to communicating with the second wireless communication device via the third beam for the first CC in accordance with the BFR RSs received via the first CC via the third beam; and wherein the beam failure recovery operation comprises switching from communicating with the second wireless communication device via the second beam for the second CC to communicating with the second wireless communication device via a fourth beam for the second CC in accordance with the BFR RSs received via the first CC via the third beam and in accordance with the first CC and the second CC both being within the group of CCs, wherein the new beam is the fourth beam.

13. The UE of claim 12, wherein the at least one processor is further configured to transmit a random access channel (RACH) preamble to the second wireless communication device in a resource associated with the received BFR RS on the third beam in accordance with identification of the third beam as being a strongest beam, wherein the RACH preamble is transmitted via a third CC of the group of CCs.

14. The UE of claim 12, wherein the at least one processor is further configured to transmit a medium access control (MAC) control element (MAC-CE) message to the second wireless communication device via a fourth CC, the MAC-CE message indicating the received BFR RS on the third beam in accordance with identification of the third beam as being a strongest beam, wherein the fourth CC is within a different group of CCs than the first CC and the second CC.

15. A method for wireless communication performed by a user equipment (UE), the method comprising:

receiving beam failure detection reference signals (BFD RSs) from a second wireless communication device via a first component carrier (CC) of a group of CCs via a first beam of a group of beams, the group of CCs further including a second CC and the group of beams further including a second beam for communication via the second CC;

detecting a beam failure of the first beam for the first CC in accordance with a number of the BFD RSs received during a first time period that have a signal strength that satisfies a threshold;

receiving beam failure recovery reference signals (BFR RSs) from the second wireless communication device via the first CC via a third beam;

switching from communicating with the second wireless communication device via the first beam for the first CC to communicating with the second wireless communication device via the third beam for the first CC in accordance with the BFR RSs received via the first CC via the third beam; and initiating a beam failure recovery operation that selects a new beam for the second CC in accordance with the detection of the beam failure of the first beam for the first CC and in accordance with the first CC and the second CC being both within the group of CCs, wherein the beam failure recovery operation comprises switching from communicating with the second wireless communication device via the second beam for the second CC to communicating with the second wireless communication device via a fourth beam for the second CC in accordance with the BFR RSs received via the first CC via the third beam and in accordance with the first CC and the second CC both being within the group of CCs, wherein the new beam is the fourth beam.

16. The method of claim 15, wherein the first beam for the first CC is the same as the second beam for the second CC.

17. The method of claim 15, wherein the second wireless communication device comprises a second UE, and wherein the group of beams are for sidelink communications between the UE and the second UE.

18. The method of claim 15, further comprising transmitting BFD RSs to the second wireless communication device via the second CC on the second beam during the first time period.

19. The method of claim 15, further comprising transmitting BFD RSs to the second wireless communication device via the first CC on one or more other beams during a second time period that is subsequent to the first time period.

20. The method of claim 19, further comprising ceasing monitoring for BFD RSs from the second wireless communication device and initiating transmission of the BFD RSs based on a number of CCs included in the group of CCs at a beginning of the second time period being less than a number of CCs included in the group of CCs at the beginning of the first time period or based on a predetermined BFD RS schedule associated with transmission of the BFD RSs by the second wireless communication device.

21. The method of claim 15, further comprising transmitting a random access channel (RACH) preamble to the second wireless communication device in a resource associated with the received BFR RS on the third beam in accordance with identification of the third beam as being a strongest beam, wherein the RACH preamble is transmitted via a third CC of the group of CCs.

22. The method of claim 15, further comprising transmitting a medium access control (MAC) control element (MAC-CE) message to the second wireless communication device via a fourth CC, the MAC-CE message indicating the received BFR RS on the third beam in accordance with identification of the third beam as being a strongest beam, wherein the fourth CC is within a different group of CCs than the first CC and the second CC.

23. A user equipment (UE) comprising:
at least one processor; and
a memory coupled with the at least one processor and storing processor-readable code that, when executed by the at least one processor, is configured to:
receive beam failure detection reference signals (BFD RSs) from a second wireless communication device via a first component carrier (CC) of a group of CCs via a first beam of a group of beams, the group of CCs further including a second CC and the group of beams further including a second beam for communication via the second CC;
detect a beam failure of the first beam for the first CC in accordance with a number of the BFD RSs received during a first time period that have a signal strength that satisfies a threshold;
receive beam failure recovery reference signals (BFR RSs) from the second wireless communication device via the first CC via a third beam;
switch from communicating with the second wireless communication device via the first beam for the first CC to communicating with the second wireless communication device via the third beam for the first CC in accordance with the BFR RSs received via the first CC via the third beam; and
initiate a beam failure recovery operation to select a new beam for the second CC in accordance with the detection of the beam failure of the first beam for the first CC and in accordance with the first CC and the second CC being both within the group of CCs, wherein the beam failure recovery operation comprises switching from communicating with the second wireless communication device via the second beam for the second CC to communicating with the second wireless communication device via a fourth beam for the second CC in accordance with the BFR RSs received via the first CC via the third beam and in accordance with the first CC and the second CC both being within the group of CCs, wherein the new beam is the fourth beam.

24. The UE of claim 23, wherein the first beam for the first CC is the same as the second beam for the second CC.

25. The UE of claim 23, wherein the second wireless communication device comprises a second UE, and wherein the group of beams are for sidelink communications between the UE and the second UE.

26. The UE of claim 23, wherein the at least one processor is further configured to transmit BFD RSs to the second wireless communication device via the second CC on the second beam during the first time period.

27. The UE of claim 23, wherein the at least one processor is further configured to transmit BFD RSs to the second wireless communication device via the first CC on one or more other beams during a second time period that is subsequent to the first time period.

28. The UE of claim 27, wherein the at least one processor is further configured to cease monitoring for BFD RSs from the second wireless communication device and initiating transmission of the BFD RSs based on a number of CCs included in the group of CCs at a beginning of the second time period being less than a number of CCs included in the group of CCs at the beginning of the first time period or based on a predetermined BFD RS schedule associated with transmission of the BFD RSs by the second wireless communication device.

29. The UE of claim 27, wherein the at least one processor is further configured to transmit a random access channel (RACH) preamble to the second wireless communication device in a resource associated with the received BFR RS on the third beam in accordance with identification of the third beam as being a strongest beam, wherein the RACH preamble is transmitted via a third CC of the group of CCs.

30. The UE of claim 27, wherein the at least one processor is further configured to transmit a medium access control (MAC) control element (MAC-CE) message to the second wireless communication device via a fourth CC, the MAC-CE message indicating the received BFR RS on the third beam in accordance with identification of the third beam as being a strongest beam, wherein the fourth CC is within a different group of CCs than the first CC and the second CC.

* * * * *